US007217928B2

(12) United States Patent
Crosetto

(10) Patent No.: US 7,217,928 B2
(45) Date of Patent: May 15, 2007

(54) METHOD AND APPARATUS FOR DETERMINING DEPTH OF INTERACTIONS IN A DETECTOR FOR THREE-DIMENSIONAL COMPLETE BODY SCREENING

(76) Inventor: Dario B. Crosetto, 900 Hideaway Pl., DeSoto, TX (US) 75115

( * ) Notice: Subject to any disclaimer, the term of this patent is extended or adjusted under 35 U.S.C. 154(b) by 0 days.

(21) Appl. No.: 11/157,313

(22) Filed: Jun. 20, 2005

(65) Prior Publication Data

US 2005/0230626 A1 Oct. 20, 2005

Related U.S. Application Data

(60) Continuation of application No. 10/934,829, filed on Sep. 2, 2004, now abandoned, which is a continuation of application No. 10/721,345, filed on Nov. 25, 2003, now abandoned, which is a division of application No. 10/376,024, filed on Feb. 26, 2003, now abandoned, application No. 11/157,313, which is a continuation-in-part of application No. 10/706,821, filed on Nov. 10, 2003, now Pat. No. 7,132,664.

(60) Provisional application No. 60/424,933, filed on Nov. 9, 2002.

(51) Int. Cl.
*G01T 1/164* (2006.01)
(52) U.S. Cl. ....................... 250/366
(58) Field of Classification Search ............. 250/366, 250/367, 368
See application file for complete search history.

(56) References Cited

U.S. PATENT DOCUMENTS 6,459,085 B1 * 10/2002 Chang et al. .......... 250/370.11

OTHER PUBLICATIONS

J. S. Huber, W. W. Moses, M. S. Andreaco, and O. Petterson, "A LSO Scintillator Array for a PET Detector Module with Depth of Interaction Measurement." IEEE Trans. Nucl. Sci., vol. 48, pp. 684-688, Jun. 2001.*

* cited by examiner

*Primary Examiner*—Constantine Hannaher
(74) *Attorney, Agent, or Firm*—Jones Day; Brett Lovejoy

(57) ABSTRACT

The present invention is directed to a system and method for efficiently and cost effectively determining an accurate depth of interaction for a crystal that may be used for correcting parallax error and repositioning LORs for more clear and accurate imaging. The present invention is directed to a detector assembly having a thin sensor (e.g., APD) deployed in front of the detector (the side where the radioactive source is located and the photon is arriving to hit the detector) and a second sensor (APD or photomultiplier) on the opposite side of the detector. The light captured by the two interior and exterior sensors which is proportional to the energy of the incident photon and to the distance where the photon was absorbed by the detector with respect to the location of the two sensors, is converted into an electrical signal and interpolated for finding the distance from the two sensors which is proportional to the location where the photon hit the detector.

18 Claims, 11 Drawing Sheets

| Time | Proc (1d) data # | Reg (1d) data # | Proc (2d) data # | Reg (2d) data # | Proc (3d) data # | Reg (3d) data # | Proc (4d) data # | Reg (4d) data # | Proc (5d) data # | Reg (5d) data # |
|---|---|---|---|---|---|---|---|---|---|---|
| 3t | 1 | | | | | | | | | |
| 4t | 1 | i2 | | | | | | | | |
| 5t | 1 | i3 | 2 | | | | | | | |
| 6t | 1 | i4 | 2 | i3 | | | | | | |
| 7t | 1 | i5 | 2 | i4 | 3 | | | | | |
| 8t | 6 | r1 | 2 | i5 | 3 | i4 | | | | |
| 9t | 6 | i7 | 2 | r1 | 3 | i5 | 4 | | | |
| 10t | 6 | i8 | 7 | r2 | 3 | r1 | 4 | i5 | | |
| 11t | 6 | i9 | 7 | i8 | 3 | r2 | 4 | r1 | 5 | |
| 12t | 6 | i10 | 7 | i9 | 8 | r3 | 4 | r2 | 5 | r1 |
| 13t | 11 | r6 | 7 | i10 | 8 | i9 | 4 | r3 | 5 | r2 |
| 14t | 11 | i12 | 7 | r6 | 8 | i10 | 9 | r4 | 5 | r3 |

FIG. 2B

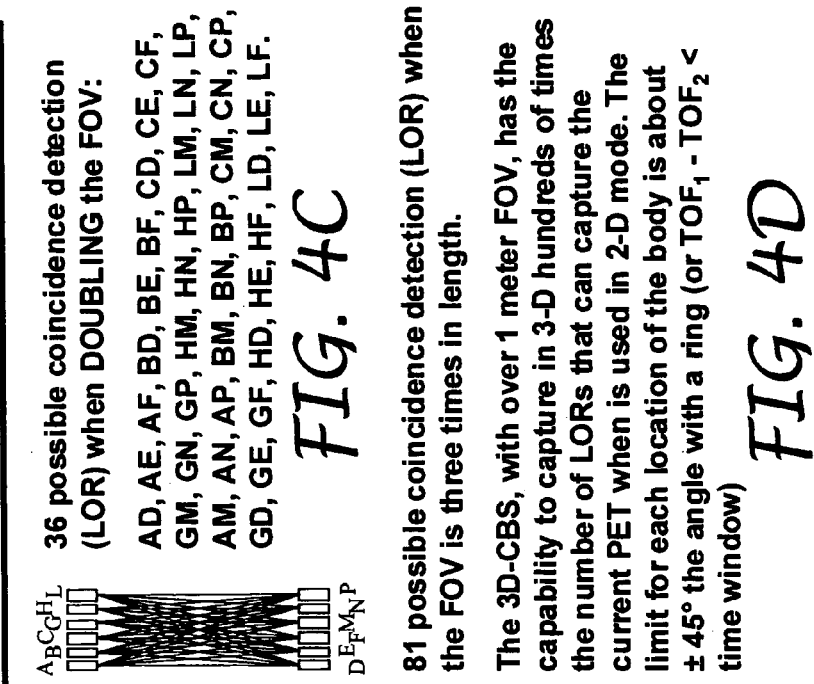
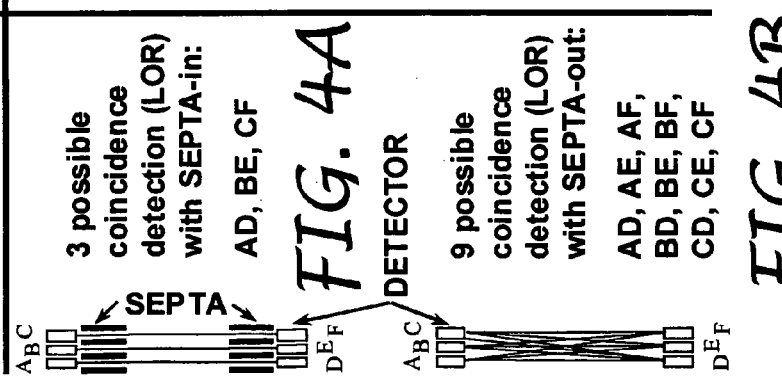
FIG. 4A  FIG. 4B  FIG. 4C  FIG. 4D

METHOD AND APPARATUS FOR DETERMINING DEPTH OF INTERACTIONS IN A DETECTOR FOR THREE-DIMENSIONAL COMPLETE BODY SCREENING

CROSS REFERENCES TO RELATED APPLICATIONS

The present application is a continuation of and claims the benefit of priority from U.S. Non-Provisional patent application Ser. No. 10/934,829, entitled "Method and Apparatus for Determining Depth of Interactions in a Detector for Three-Dimensional Complete Body Screening," filed on Sep. 2, 2004 now abandoned; which is a continuation of and claims the benefit of priority from U.S. Non-Provisional patent application Ser. No. 10/721,345, entitled "Method and Apparatus for Determining Depth of Interactions in a Detector for Three-Dimensional Complete Body Screening," filed Nov. 25, 2003 now abandoned; which is a divisional of, and claims the benefit of priority from U.S. Non-Provisional Patent Application entitled, "Method and Apparatus for Three-Dimensional Complete Body Screening," having application Ser. No. 10/376,024, and filed on Feb. 26, 2003,now abandoned, for inventions not disclosed in U.S. Provisional No. 60/360,301. Therefore, the present application does not seek benefit from U.S. Provisional No. 60/360,301 for the subject matters not disclosed therein. The present application is also a continuation in part of, and claims the benefit of priority from U.S. Non-Provisional patent application entitled, "Method and Apparatus for Improving Pet Detectors," having application Ser. No. 10/706,821, and filed on Nov. 10, 2003,now U.S. Pat. No. 7,132,664, which claims priority to U.S. Provisional Patent Application No. 60/424,933, of the same title and filed on Nov. 09, 2002 and each of which is incorporated by reference herein in its entirety.

The present application is also related to the following patent applications:

U.S. Pat. No. 5,937,202 filed Feb. 15, 1996 entitled "High-Speed, Parallel, Processor Architecture for Front-End Electronics, Based on a Single Type of ASIC, and Method Use Thereof."

U.S. patent application Ser. No. 09/506,207 filed Feb. 15, 2000 entitled "Method and Apparatus for Extending Processing Time in One Pipeline Stage," which claims priority from: U.S. Provisional Patent Application No. 60/120,194 filed Feb. 16, 1999; U.S. Provisional Patent Application No. 60/112,130 filed Mar. 12, 1999; U.S. Provisional Patent Application No. 60/129,393 filed Apr. 15, 1999; U.S. Provisional Patent Application No. 60/132,294 filed May 3, 1999; U.S. Provisional Patent Application No. 60/142,645 filed Jul. 6, 1999; U.S. Provisional Patent Application No. 60/143,805 filed Jul. 14, 1999; U.S. Provisional Patent Application No. 60/154,153, Sep. 15, 1999; U.S. Provisional Patent Application No. 60/161,458 filed Oct. 25, 1999; U.S. Provisional Patent Application No. 60/164,694 filed Nov. 10, 1999; and U.S. Provisional Patent Application No. 60/170,565 filed Dec. 14, 1999.

U.S. patent application Ser. No. 10/185,904 filed Jun. 27, 2002 entitled "Method and Apparatus for Whole-Body, Three-Dimensional Dynamic PET/CT Examination," claiming priority from U.S. Provisional Patent Application No. 60/301,545 filed Jun. 27, 2001; and U.S. Provisional Patent Application No. 60/309,018 filed Jul. 31, 2001.

U.S. patent application Ser. No. 10/296,532 filed Nov. 25, 2002 entitled "Method and Apparatus for Anatomical and Functional Medical Imaging," which claims priority from: PCT/US01/15671 filed May, 15, 2001; U.S. Provisional Patent Application No. 60/204,900 filed May 16, 2000; U.S. Provisional Patent Application No. 60/215,667 filed Jun. 30, 2000; U.S. Provisional Patent Application No. 239, 543 filed Oct. 10, 2000; U.S. Provisional Patent Application No. 60/250,615 filed Nov. 30, 2000; U.S. Provisional Patent Application No. 60/258,204 filed Dec. 22, 2000; and U.S. Provisional Patent Application No. 60/261,387 filed Jan. 15, 2001.

U.S. patent application Ser. No. 10/376,024 filed Feb. 26, 2003 entitled "Method And Apparatus For Determining Depth of Interactions in a Detector for Three-Dimensional Complete Body Screening," claiming priority from U.S. Provisional Patent Application No. 60/360,301 filed Feb. 26, 2002.

U.S. patent application Ser. No. 10/453,255 filed Jun. 2, 2003 entitled "Gantry for Geometrically Configurable and Non-Configurable Positron Emission Tomography Detector Arrays," claiming priority from U.S. Provisional Patent Application 60/385,140 filed Jun. 2, 2002.

The above-identified patent applications are incorporated by reference herein in their entireties.

BACKGROUND OF THE INVENTION

1. Field of the Invention

The present invention relates to radiation detectors. More particularly, the present invention relates to a system and method for correcting parallax error in a detector resulting from inaccurately assessing where the photon interacted with the detector, and thereby increasing efficiencies of traditional Positron Emission Tomography (PET) devices on a photons per unit of radiation basis.

2. Description of Related Art

These devices (detectors) are about 200 times smaller than the large detectors for high-energy physics and require identification of only one particle, the photon. The task to be solved of capturing and identifying the particles is relatively easier than before: one particle instead of five on a detector 200 times smaller.

The use of positron emissions for medical imaging has been well document from the early 1950's, see "A History of Positron Imagining," Brownell, Gordon, presented on Oct. 15, 1999, Massachusetts General Hospital, which is incorporated herein by reference in its entity. PET imaging has advantages over other types of imaging procedures. Generally, PET scanning provides a procedure for imaging the chemical functionality of bodily organs rather than imaging only their physical structure, as is commonly available with other types of imaging procedures such as X-ray, Computerized Tomography (CT), or Magnetic resonance imaging (MRI). PET scanned images allow a physician to examine the functionality heart, brain, and other organs as well as diagnosing disease groups which cause changes in the cells of a body organ or in the manner they grow, change, and/or multiply out of control, such as cancers.

Positron Emission Tomography (PET) is a medical imaging technique that involves injecting a natural compound, such as sugar or water, labeled with a radioactive isotope into a patient's body to reveal internal biological processes. As the isotope (positron) circulates within the patient's body. The positron annihilates with and electron and emits pairs of photons in diametrically opposed directions (back-to-back). A PET device is made of a set of detectors coupled to thousands of sensors that surround the human body. These detectors (crystals) capture the photons emitted by the isotope from within the patient's body at a total rate of up to hundreds of millions per second, while the sensors (transducers such as PMTs) convert them to electrical signals, and send the signals to the electronics.

Other applications for detecting particles (photons, electrons, hadron, muon and jets) are well known, such as with regard to experiments in high energy physics. While particle detection in high energy physics and medical imaging have some common ground, differences between the disciplines exist. One distinction between the usages is that the detectors used in medical imaging are approximately 200 times smaller than the larger detectors employed in high-energy physics applications. Moreover medical imaging PET applications require the identification of only a single type of particle, the photon.

Typically, prior art Positron Emission Tomography (PET) devices require the injection into the patient's body of a radiation dose that is 10 to 20 times the maximum radiation dose recommended by the International Commission on Radiological Protection (ICRP). This amount is necessary because, at best, prior art PET devices only detect 2 photons out of 10,000 emitted in the patients' body. Currently the largest manufacturers of PET (General Electric Company and Siemens AG (ADR)) which command in excess of 90% of the world market, are manufacturing two different PET (PET/CT) systems with very similar performance and are selling them at very similar prices. However, although the price and performance of the systems from the different manufactures are comparable, one manufacturer's system (Siemens) uses nearly ideal crystal detectors, while contrastingly, the other manufacturer's system (General Electric) uses cheaper, lower quality crystal detectors with slower decay time. Consequently, the manufacturer using the cheaper, lower cost detectors, expend on the order of only 10% the price of the ideal crystals used in their competitor's systems. Thus, the question arises: how it could be that even though one manufacturer uses crystals detectors that are ten times more expensive that the other manufacturer, the price and performance of the two PET systems from the different manufacturers are very comparable.

Anecdotally, the present inventor has analyzed the progress of the most significant PET improvements made in the most recent 17 years, see "400+ times improved PET efficiency for lower-dose radiation, lower-cost cancer screening," 3D-Computing, Jun. 30, 20010, ISBN: 0970289707, which is incorporated herein by reference in its entity. During that time period the efficiency of PET improved at a rate of between two and three times every five years. The analysis included technical literature, patents (including those assigned to GE and Siemens) and also PETs that were built as prototypes at several universities but were never commercialized. At the current improvement rate of PET advancement, conservatively it would take several decades of improvements for the radiation dose necessary for a PET procedure to come within the maximum radiation dose recommended by the ICRP.

What is needed is a means for increasing the accuracy and efficiencies of PET devices, enabling caregivers to more accurately diagnose ailments related to the functionality of body organs and not just inferences from the structure of the organs. Additionally, what is needed is a quantum advance forward in PET devices and procedures wherein patients can receive the benefits of PET imaging without the associative risks from the radioactive doses necessary for the procedures. Finally, what is needed is a means for reducing the associated risks and increasing detection efficiencies associated with PET imaging procedures to such an extent that the benefits of PET imaging can be applied in well body care and preventative medicine strategies for apparently healthy individuals; as a standard health assessment and diagnostic tool for regular, periodic checkups.

SUMMARY OF THE INVENTION

The present invention is directed to a system and method for efficiently and cost effectively determining an accurate depth of interaction for a crystal that may be used for correcting parallax error and repositioning LORs for more clear and accurate imaging. The present invention is directed to a detector assembly having a thin sensor (e.g. an Avalanche Photodiode (APD)) is deployed in front of the detector (side where the radioactive source is located and the photon is arriving to hit the detector) and a second sensor (APD or photomultiplier) on the opposite side of the detector. The light captured by the two sensors interior sensor and exterior sensor, which is proportional to the energy of the incident photon and to the distance where the photon was absorbed by the detector with respect to the location of the two sensors, is converted into electrical signal and interpolated for finding the distance from the two sensors, which is proportional to the location where the photon hit the detector.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIGS. 2A–2C are diagrams of the sequence of operations in a 3D-Flow sequentially implemented parallel-processing architecture in accordance with exemplary embodiments of the present invention;

FIGS. 4A–4D are diagrammatical comparisons of the relationship between the increasing FOV in LOR in accordance with exemplary embodiments of the present invention;

Figure 1:
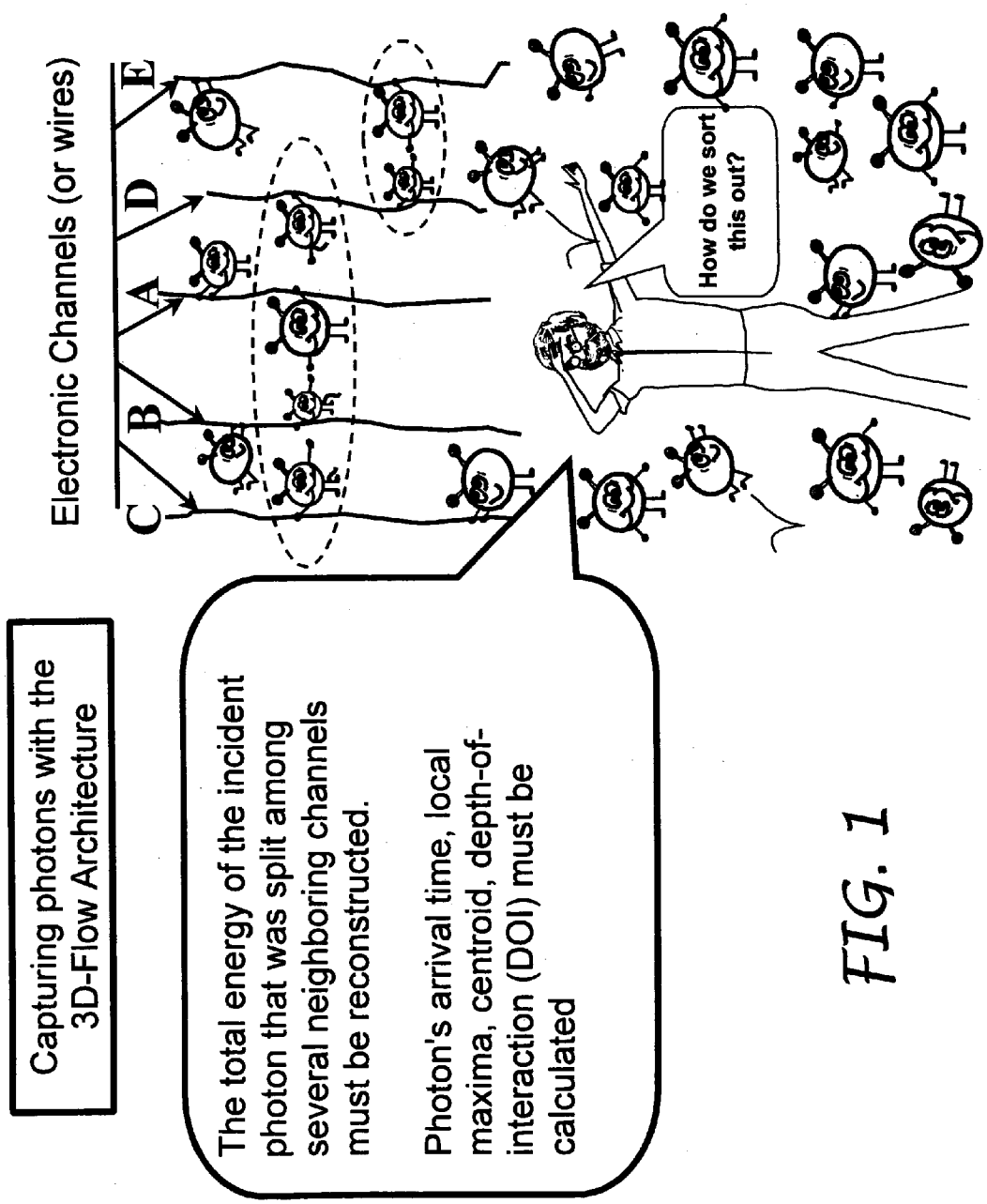
FIG. 1 is a diagram depicting the arrival of information about the particles from several electronic channels at one time in accordance with an exemplary embodiment of the present invention.

Other features of the present invention will be apparent from the accompanying drawings and from the following detailed description.

DETAILED DESCRIPTION OF THE INVENTION

The present invention relates to improvements in processing data acquired from sensors coupled to detectors, enabling the alteration of altering detector placement, detector array spacing and detector field of view for increasing the capture rates of photons, and thereby increasing efficiencies of traditional Positron Emission Tomography (PET) devices on a photons per unit of radiation basis. It is a method and apparatus consisting of:
  a) A detector of photons covering a large surface of a human body (field of view—FOV);
  b) A particular detector assembly that best couples and transfers to the transducer and electronics the information generated by the interaction of a photon with the detector.
  c) An electronics with the capability to process most information arriving from the detector without the limitation of saturation or processing dead-time for any given radiation to the patient.

The electronics can acquire data faster than the decay time of any specific detector (e.g. crystals), it can process the data captured by all detector/transducer elements at a specific time (synchronous or asynchronous) in parallel form, it can execute different programmable real-time algorithms on the acquired data, each algorithm suitable to a different detector for best extraction of all parameters of the interaction of the photon with the detector. When the processing time is longer than the time interval between two consecutive sets of input data, the electronics route the received information to a different set of processors via bypass switches. A particular arrangement of processor arrays and bypass switches are implemented in a hardware system made of boards and chassis (VME or IBM PC). This electronics compared to the prior art electronics used by other inventors/manufacturers, although has intrinsic features and advantages that improve sensitivity of current PET, however, when:
  a) coupled to a detector which is assembled differently from the assembly used in current PET, and when
  b) coupled to a transducer array which is in a different relation and array segmentation compared to the one used in current PET,
    has the capability to extract more accurately, more information from the interaction of the photons with the detector, allowing:
    1. to capture more accurately more photons emitted by the patient's body (which allow to improve the sensitivity of current PET and which allows to increase the length of the detector in a cost-effective manner, thus allowing a further great increase of the sensitivity of the instrument and thus it allows to reduce the radiation to the patient),
    2. to use more economical crystals (which reduces detector cost),
    3. to accurately measure the depth of interaction by using two sensors on both sides of the detector (which improves spatial resolution),
    4. to measure more accurately the energy of the incident photon (which allows to reject more accurately scatter events and thus reduce "false positives" and "false negatives", and
    5. to measure more accurately the location of the incident photon (which improves spatial resolution).

This inventions enables:
  a) to use a PET device for preventive health care screening. (Without this invention, current PET cannot be used in preventive health care screening because they require to deliver to the patient 20 to 30 times the radiation accepted by the International Commission for Radiation Protection)
  b) to have a revolutionary change in the way images will be displayed (The image resulting from an examination with the 3-D Complete Body Screening tool (3D-CBS) is three dimensional, visualizes the whole body at one time, because data are recorded at the same time over the entire body, and has greatly increased definition. It provides dynamic imaging, allowing for motion studies of real-time metabolic activity. The 3D-CBS has the unique capability of recording data continuously and simultaneously over the entire body. This makes it possible to view images of biological processes, blood flow, and organ movements as a running film instead of a static picture. Current PET cannot provide this because the information is acquired at different time in different section of the body. No more slices of the body, but real 3-D images of any organ of the body. No more need to take several cancer screening examinations, but only a single, more efficient examination that will detect not only cancer, but also other diseases).
  c) it will lower the cost of health care because more economical crystals can be used with this innovative technology. This will lower the examination cost and will combine in a single exam the examination of many organs, elimination the need of several, different, expensive (and sometimes invasive) of screening for cancer such as mammogram, colonoscopy, etc.
  d) it will be an essential tool to develop and study the effect of new, experimental pharmacopeia.

The cumulative effect of the combination of improvements disclosed herein yields increased detection efficiencies to the extent necessary to reduce the reducing the associated risks and associated with PET imaging procedures to such an extent that the benefits of PET imaging can be realized with radiation dosages far less than that recommended by the International Commission on Radiological Protection (ICRP). Thus, PET imaging can be realized as a standard health assessment and diagnostic tool for regular, periodic checkups in conjunction with well body care and preventative medicine plans for apparently healthy individuals. Moreover, because the present invention realizes a substantial increase in detection efficiencies, more comprehensive and higher quality PET images are obtainable in substantially less time than is required for prior art PET imagining procedures, consuming far less radioactive materials. Consequentially, the present invention allows for substantially more procedures to be performed in the time period as a single prior art PET procedure. Thus, even factoring the in additional support and diagnostic personnel necessary for the additional procedures, the cost per scan procedure is far less than prior art imaging techniques.

In the year 2001 the two major companies in the field introduced four new machines which were the result of their planning before innovation appeared in "400+ Times Improved PET Efficiency For Lower-Dose Radiation, Lower-Cost Cancer Screening," 3D-Computing, Jun. 30, 20010, ISBN: 0970289707 (hereinafter 400+ Times). These machines are a PET/CT called "Biograph" by Siemens, one called "Discovery LS" from GE, a new PET called "ECAT ACCEL" from Siemens, and a new PET from GE called "Advance Nxi." All the above new machines had a field of view (FOV, length of the detector) of about 16 cm. This followed the previous trend of limiting the capturing of photons and requiring high radiation to the patient. (The new PET from Siemens even showed a step backwards in FOV from their previous model "EXACT3D" which had 25 cm FOV). An indication of the revolution caused by the advent of the new discovery described herein and in other U.S. and international patents that the direction shown by the large companies in the year 2001 will reverse in the year 2002 and in the coming years. It is expected that the above identified companies (and new companies) following the trend introduced with this discovery: they will increase the FOV instead of decreasing it as taught by the present inventor in co-pending U.S. Non-Provisional patent application Ser. No. 10/296,532, entitled "Method And Apparatus For Anatomical And Functional Medical Imaging," relating to and claiming priority from PCT/US01/1567160/204,900, filed May 15, 2001 which relates to and claims priority from U.S. Provisional Patent Application No. 60/204,900 filed May 16, 2000, U.S. Provisional Patent Application No. 60/215,667 filed Jun. 30, 2000, U.S. Provisional Patent Application No. 60/239,543 filed Oct. 10, 2000, U.S. Provisional Patent Application No. 60/250,615 filed Nov. 30, 2000, U.S. Provisional Patent Application No. 60/258,204 filed Dec. 22, 2000 and U.S. Provisional Patent Application No. 60/261,387 filed Jan. 15, 2000 which are each incorporated herein by reference in their entirety (see also 4000+ Times by the present inventor). In fact, the new PET model called Discovery VI just introduced by GE has a longer FOV of 50 cm and is using crystal detectors even cheaper than the one used before. This improvement is still far from reaching the level of efficiency achieved by the inventor's design and described in U.S. patent application Ser. No. 10/296,532 and its prodigy, because the new GE PET has still a resolution of about 6 mm, which is lower than the previous PET, and a coincidence window of about 12 nanosecond, which is longer than previous PET.

It will take time and involve technological change, replacing the display of information in slices by real-time 3-D over the entire body, and the obsolescence of gamma camera, SPECT and all such equipment that captures only 1 out of 300,000 photons. These, and other parameters listed below are achieved by the present invention:

radiation lowered from 1100 mrem per exam to less than 100 mrem acceptable to the ICRP and which will allow screening without hazard to the patient);

the quality of the picture is improved from the capture of about 60 million pairs of photons per examination in more than one hour (with Fluorodeoxyglucose—FDG) to about 240 million in 4 minutes. (The identification of the photons also improves, improving the image quality, with the reconstruction of the total energy of photons in the 3D-CBS; this is not performed in prior art PET)

the cost of one examination can be realized from the current cost of $2,000–$4,000 per exam to about $400 per exam The new GE PET Discovery VI with 50 cm FOV, about 6 mm resolution, about 12 nanosecond coincidence window, and with no significant advantage in lower radiation and lower examination price is still far from reaching those goals (some parameters are even worse than previous PET).

The ICRP and the U.S. National Council on Radiation Protection and Measurements (NCRP) recommends a limit of 100 mrem per year (average over five years) of exposure to ionizing radiation for the general population (ICRP Publication 60, Annuals of the ICRP 21, pp. 25; 1991 and Ordonnance sur la radioprotection (OraP) Le conseil federal suisse. 19 Dec. 2000). A single PET (or CT) examination using devices currently available in hospitals gives the patient 10 to 20 times this dose.

Prior art PETs require a high radiation dose to the patients because they can capture only a few of the photons emitted from the patient's body: at most they can capture about two out of 10,000 photons emitted. The sensitive area of the prior art detector that can capture photons (the axial field of view (FOV), or the length of the detector) covering the patient's body is very small and the electronics inefficient. Until now, the greatest impediment to extending the FOV has been the electronics of prior art PET, which could not efficiently capture the photons and was saturating with even the short FOV.

The unique architecture of the presently described invention in the embodiment of the 3D-CBS electronics permits the extension of the FOV to over one meter in length and captures about 1,000 out of 10,000 photons in time coincidence. The innovations that reduce the required radiation to the patient to $\frac{1}{30}$ of current requirement lie partly in the way existing components (available off the shelf) are assembled together with the innovative section of the electronics (the 3D-Flow system). Such technology allows:

1. an increase in the input bandwidth of the electronics from the 10 million events per second of prior art PET to over 36 billion in the 3D-CBS PET (a high bandwidth of the electronics is required because the photons arrive at the detector randomly) as described in co-pending U.S. Non-Provisional patent application No. 10/185,904 entitled "Method And Apparatus For Whole-Body, Three-Dimensional, Dynamic PET/CT Examination," filed on Jun. 27, 2002 by the present inventor, relating to and claiming priority from U.S. Provisional Patent Application No. 60/301,545, filed Jun. 27, 2001, Ser. No. 60/301,545, entitled Method And Apparatus For Whole-Body Annual PET/CT Examination, and U.S. Provisional Patent Application No. 60/309,018 entitled "Method And Apparatus For Whole-Body, Three-Dimensional, Dynamic PET/CT Examination," which are each incorporated herein by reference in their entirety. (See also Section 4 of Crosetto, D. "Saving lives through early cancer detection: Breaking the prior art PET efficiency barrier with the 3D-CBS" (referred to as "Saving Lives" hereinafter);

2. an increase in the field of view to over one meter, providing good efficiency in photon detection (e.g. a 3D-CBS with only three times the FOV of prior art PET could detect nine times the number of photons compared to prior art PET when they are used in 3-D and 27 times when prior art PET are used in 2-D mode); and 3. the accurate identification of most photons, using digital signal processing with neighboring data exchange performed by a set of DSPs on each electronic channel. Each DSP executes a complex real-time photon detection algorithm, as taught in patent application Ser. No. 10/185,904 (see also FIG. 34 in Saving Lives).

This 3D-Flow architecture has been designed in intellectual property (IP) form, suitable to be targeted to several technologies, and has been built into field programmable gate array (FPGA) (2.6 million gates 0.18 micron CMOS technology, 8 aluminum layers) with four 3D-Flow processors in a single chip as described in co-pending U.S.

Non-Provisional patent application Ser. No. 09/506,207 entitled "Method And Apparatus For Extending Processing Time In One Pipeline Stage," filed Feb. 16, 2000 by the present inventor, relating to and claiming priority from claiming U.S. Provisional Patent Application No. 60/120,194, entitled "Implementation of Fast Data Processing With Mixed-Signal And Purely Digital 3D-Flow Processing Boards," filed Feb. 16, 1999, U.S. Provisional Patent Application No. 60/112,130, entitled "Design Real-Time," filed Mar. 12, 1999, U.S. Provisional Patent Application No. 60/129,393, entitled "Novel Instrumentation For Pet With Multiple Detector Types," filed Apr. 15, 1999, U.S. Provisional Patent Application No. 60/132,294, entitled "System Design And Verification Process For Electronics," filed May 3, 1999, U.S. Provisional Patent Application No. 60/142,645, entitled "Real-Time System Design Environment For Multi-Channel High-Speed Data Acquisition System And Pattern-Recognition," filed Jul. 6, 1999, U.S. Provisional Patent Application No. 60/143,805, entitled "Design And Verification Process For Breaking Speed Barriers In Real-Time Systems," filed Jul. 14, 1999, U.S. Provisional Patent Application No. 60/154,153, entitled "Novel Idea That Can Bring Benefits In Proven HEP Applications," filed Sep. 15, 1999, U.S. Provisional Patent Application No. 60/161,458, entitled "System Design And Verification Process For LHC Trigger Electronics," filed Oct. 25, 1999, U.S. Provisional Patent Application No. 60/164,694, entitled "Advantages Of The 3D-Flow System Compared To Current Systems," filed Nov. 10, 1999, and U.S. Provisional Patent Application No. 60/170,565, entitled "Novel Instrumentation For PET/SPECT Suitable For Multiple Detector Types," filed Dec. 14, 1999 each filed by the present inventor and are each incorporated herein by reference in their entirety by the present inventor which is incorporated herein by reference in its entirety (see also "LHCb Base-Line Level-0 Trigger 3D-Flow Implementation," Nuclear Instruments and Methods in Physics Research, Section A, vol. 436 (November 1999) pp. 341–385 (referred to as "LHCb Base-Line" hereinafter). Full simulations of the system with fault-tolerant capabilities have been performed for the entire system. A hardware prototype implementing these functions in real time, using Altera's FPGA described in patent application Ser. No. 09/506,207 (also described in "Proven Technology for the New 3D Complete-Body-Scan (3D-CBS) Medical Imaging Device," 3D-CBS Progress report (November 2001) pp. 1–4 presented at the seminar at the Industrial Program of the IEEE Nuclear Science Symposium and Medical Imaging Conference at San Diego, Calif., U.S., on Nov. 6, 2001 (referred to as "Proven Technology" hereinafter, www.3d-computing.com/pb/report1.pdf). These publications demonstrate its hardware feasibility. This hardware construction is the basic element of the project and is described in, for example, The Changing of Positron Imaging System. Clinical Positron Imaging, "by Phelps, M. E. et al. in" vol. 1(1): 31045, 1998. Several of these basic elements replicated hundreds of times makes the electronic system of the 3D-CBS. The staging of the construction of the 3D-CBS is also presented herein, and taught by Crosetto in U.S. Pat. No. 5,937,202 entitled "High-Speed, Parallel, Processor Architecture for Front-End Electronics, Based on a Single Type of ASIC, and Method Use Thereof," and also in patent application 09/506,207 (see also Saving Lives).

The present invention is predicated on advancements in PET systems, circuitry, detectors, processors and processing architectures described in patent application Ser. No. 09/506,207 (see also LHCb Base-Line). Full simulations of the system with fault-tolerant capabilities have been performed for the entire system.

The new discovery was first described logically and compared to the existing technology. Then was analyzed and proven by computer simulation, the results of which were published in Nuclear Instrument and Methods in Physics Research (see vol. 436 (1999) pp. 341–385). Recently the electronics, which is directed to efficiency, has been implemented in hardware in field-programmable gate array (FPGA), Altera 20K1000, (see also Proven Technology"). The other elements of the new 3-D Complete Body Screening (3D-CBS) design (detector, software reconstruction, etc.) are available as off-the-shelf components and therefore an operable embodiment is possible, while the improvements to the off-the-shelf components to take advantage of the additional information provided by the 3D-CBS, which acquires more accurate data at the same time over the entire body, are formulated in the future. This will allow to reconstruct a real three dimensional object of all organs and of all body.

The more noteworthy improvements the 3D-CBS offers over the prior art PET are: (a) capturing more data from the emitting source and (b) processing the acquired data with a real-time algorithm which best extracts the information from the interaction between the photons and the crystal detector.

If more data from a radioactive source at the level of radiation currently used (or from a source with lower radiation activity) is captured by the detector, sent to the PET electronics, and processed correctly, then the examination time, radiation dosage, and consequently also the cost per examination can be significantly reduced. In order to obtain more data, the axial field of view (FOV, the total length of the rings of crystals in the PET detector) must be lengthened to cover most of the body. In order to process these data, the electronics must be designed to handle a high data input rate from multiple detector channels. The 3D-CBS can handle up to 35 billion events per second with zero dead time in the electronics versus the 10 million events per second with dead time that the prior art PET can hand (using a system with 1,792 channels as described by Crossetto in patent application Ser. No. 10/296,532 (Method And Apparatus For Anatomical And Functional Medical Imaging) (see also "A Modular VME or IBM PC Based Data Acquisition System For Multi-Modality PET/CT Scanners Of Different Sizes And Detector Types," presented at the IEEE Nuclear Science Symposium and Medical Imaging Conference, Lyon, France, 2000, IEEE-2000-563, (hereinafter referred to as "Modular VME,". High input bandwidth of the system is necessary because the photons arrive at random time intervals.

Crossetto further describes both: (a) a novel architectural arrangement of connecting processors on a chip, on a Printed Circuit Board (PCB), and on a system; and (b) a new method of thoroughly processing data arriving at a high rate from a PET detector using the 3D-Flow sequentially-implemented parallel architecture, in patent application Ser. No. 10/296,532 (Method And Apparatus For Anatomical And Functional Medical Imaging) and in patent application Ser. No. 09/506,207 (see also Modular VME and LHCb Base-Line).

Put simply, the processing of the electronics on the data arriving from the detector can be compared to the task of reuniting families that have been separated by a catastrophic natural event, i.e., the family reunion paradigm. The following analogy in human terms is made: the two groups of signals generated by the sensors, that are coupled to the detectors hit by the two back-to-back photons of a single event are similar to the two halves of a families split apart, the mother with some of her children being separated far from her husband with the other children. The task of the detector is to find the back-to-back photons that came from the same annihilation event, or to reunite the two half families. The sequence of events in the family reunion example is one billion times slower than the sequence of annihilation events in the PET:

A catastrophic event separates on average 17 families every 50 seconds. During the attempt to reunite the families, unfortunately, only about 12% of the husbands and wives can arrive at a reunion center. The reduction of families is analogous to the reduction of photons that are absorbed by the patient's body, or not captured by the detector because of the limited field of view (FOV) and solid angle of the detector.

When a family was split, the husband and wife went in opposite directions, each with some of their children. In the analogy, the children in neighboring paths and the parent represent signals on neighboring sensors (or electronic channels) that have been generated by a photon striking the detector. The analogy illustrates the fact that the total energy of the incident photon that was split among several neighboring electronic channels must be reconstituted, just as the children must be first reunited with the parent.

The family reunion takes place in two phases. During the first phase, the father and the children who went with him but followed a neighboring path are reunited. The same process is followed independently, in a separate venue, by the mother with their other children; however, that takes place far from where the father is. During the second phase the two half-families are reunited.

FIG. 1 shows an example of information split over several channels (or wires). FIG. 1 depicts the "Family reunion" paradigm used herein. A solution, that identifies family members and checks in detail for their characteristics, is needed for the reunion of the families. The figure shows an example of the arrival of information about the particles from several electronic channels at one time. As an analogy, several members of a family arriving at the same time on different channels (e.g., see four members of a family in the second row from top) are compared to a photon that has its energy split among several electronic channels. (The size of a family member is proportional to the area of the signal in a given example).

A photon striking in such a way that its information is divided among several electronic channels is analogous to one parent with some children going down several paths. (See on the second row of the FIG. 1 in the dotted lines, the split of a family among four paths, or wires, and on the third row the split of a family between two wires).

Because there are on average about four groups of fathers with their children (or mothers with their children) arriving 26 at random time intervals every 50 seconds at any place in the 1,792 channels at the reunion center, it is necessary to clearly identify family members and reunite the half-family (or to rebuild the energy of the incident photon) at their arrival site, before the children are mixed with millions of unrelated people.

The first problem involves reuniting the half-family (rebuild the energy of each incident photon, determine its exact arrival time, measure the exact position of its center of gravity, measure the Depth of Interaction (DOI), and resolve pile-up). The solution to the problem, which is illustrated in the image of the "family reunion" of FIG. 2A, is mainly provided by the "bypass switch" (or multiplexer) of the 3D-Flow architecture (see FIG. 2B and FIG. 2C). Information concerning the father and children, that is, the signals generated by the photon, arrives at the top of the channel (wire) and moves down one step each time new data arrive at the input. The numbers in FIG. 2A correspond to the positions of the objects (data set or smiling face) at time $13t$ of FIG. 2B. Objects outlined in dotted lines correspond to the status one instant before time "$13t$."

Figure 2C:
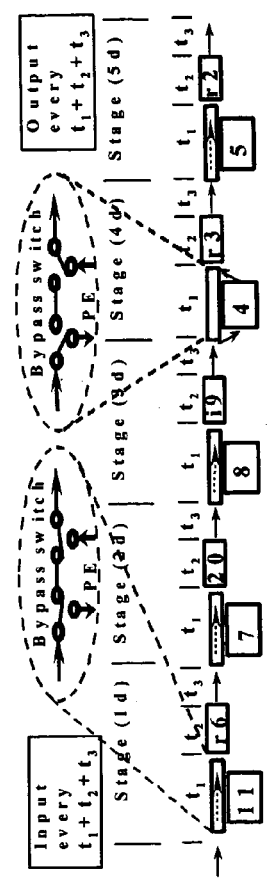
Figure 2A:
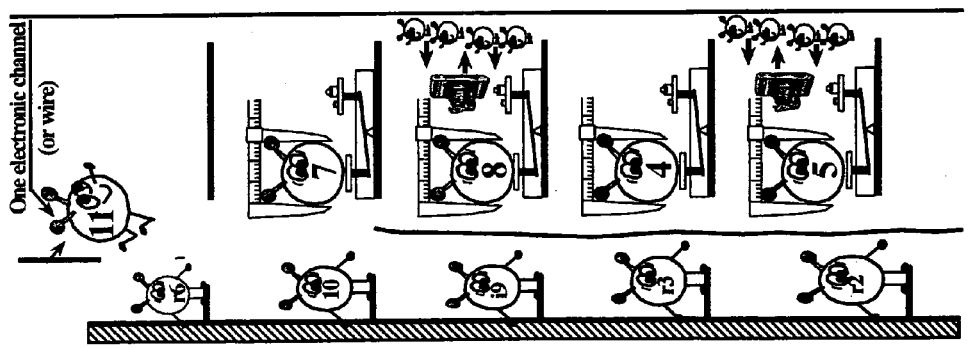

With more specific reference to FIG. 2, the illustration is subdivided into three discrete parts. FIG. 2A (left side) depicts an illustration of the "family reunion" paradigm for time $13t$ of FIGS. 2B and 2C. Each photon remains in the measuring station (processor) for a duration five times longer than the time interval between two consecutive input data. The result from any measuring station will not be an input to the next station (as it is in a typical pipeline system) but will be passed on with no further processing in the 3D-Flow sequentially implemented, parallel-architecture until it exits (see description below).

FIG. 2C (lower right side) depicts an illustration of the stages $1d$–$5d$ of the input data and output results in the registers of the 3D-Flow pipelined system at a time $13t$. The depicted example demonstrates how the 3D-Flow system extends the execution time in a pipeline stage beyond the time interval between two consecutive input data (sequentially-implemented, parallel architecture). An identical circuit (a 3D-Flow processor) is copied 5 times at stage d (the number of times the circuit is copied corresponds to the ratio between the algorithm execution time and the time interval between two consecutive input data). A bypass switch (or multiplexer) coupled to each processor in each 3D-Flow stage $1d$, $2d$, $3d$, $4d$, and $5d$ sends one data packet to its processor and passes four data packets along to the next stage ("bypass switch"). Thus, the execution time at each substation d will be $t_p=4(t1+t2+t3)+t1$. The numbers in the rectangles below the switches identify the input data packets to the CPU of the 3D-Flow processor. (See also FIG. 2B for the sequence of operations during the previous clock cycles). A 3D-Flow processor is shown in the figure with the three functions of (a) a bypass switch (dotted right arrow in the rectangle), (b) an output register (rectangle to the right), and (c) a CPU (rectangle below).

FIG. 2B (upper right side) is a tabular listing depicting a sequence of the data packet at different times in the pipeline stage (see FIG. 2C). One data packet in this application contains 64-bit information from one channel of the PET detector. The clock time at each row in the first column of the table is equal to $t=(t_1+t_2+t_3)$ of FIG. 2C. The number in the lower position in a cell of the table is the number of the input data packet that is processed by the 3D-Flow processor at a given stage. The values in the raised position, indicated as ix and rx, are the input data and the result data, respectively, which flow from register to register in the pipeline to the exit point of the system. Note that input data 1 remains in the processor at stage $1d$ for five cycles, while the next four data packets arriving (i2, i3, i4, and i5) are passed along (bypass switch) to the next stage. It should be understood that, although not shown in FIG. 2B, at last clock ($14t$), while stage $4d$ is fetching 9, it is at the same time, outputting r4. This r4 value is then transferred to the exit of the 3D-Flow system without being processed by any other d stages. Note, however, that clock $13t$ shows the status represented in FIG. 2C and that input data and output results are intercalculated in the registers of the 3D-Flow pipelined system.

The 3D-Flow architecture allows a high throughput at the input because (a) each data packet relative to the information about the photon (or about the family member) has to move only a short distance at each step, from one station to the next, and (b) complex operations of identification and measurement can be performed at each station for a time longer than the time interval between two consecutive input data.

Every time a new data packet arrives at the top of the channel, all other data packets along the vertical wire move down one step, but the wire is broken (equivalent to a bypass switch in input/output mode) in one position where the station is free to accept a new input data packet and is ready to provide at the same time the results of the calculations of the previous data packet.

At any time, four switches in "bypass mode" and one switch in "input/output mode" (or the wire broken at a different place) are always set on the vertical wire. This synchronous mechanism will prevent losing any data at input and will fully process all of them.

When a data packet relative to a photon enters a measuring station (that is, a 3D-Flow processor, or the station represented on the right side of FIG. 2A), it remains in that station for its complete identification, measurements, and correlation with its neighbors. Several operations are performed at each station:

1. A "picture" is taken and sent along with the time of arrival to the neighbors, while "pictures" from the neighbors, along with their time of arrival are also received and checks are performed to see if there were any family members in the neighboring channels. Similarly, the energy and arrival time of photons are exchanged between neighboring elements to check if the energy of the incident photon was fragmented between several channels.
2. Local maxima (checking to see if the signal is greater than the neighbors) are calculated to determine if the parent arrived at that channel; this is equivalent to comparing the photon's energy and arrival time to similar information in the neighboring channels. If the parent did not arrive at that channel, the process at that channel is aborted to avoid duplication. The neighboring channel that finds the father will carry on the process.
3. Center of gravity is calculated (that is the point at which the weight, (or photon's energy in this specific case) of an object is equally distributed). This calculation will provide an accurate location where the half-family was found; this is equivalent to the spatial resolution of the incident photon.
4. Pile-ups, which occur when two half-families belonging to two different families arrive within a very short time interval, or when two events occur in a nearby detector area within a time interval shorter than the decay time of the crystal. When this happens, the apparent integral of the second signal will show it riding on the tail of the previous signal. Digital Signal Processing (DSP) techniques of the 3D-Flow processor can detect the change of slope of the tail of the signal and separate the two signals.
5. The accurate arrival time of the half-family group is calculated and assigned to be carried for the rest of the trip. Similarly, the accurate arrival time of the photon is calculated.
6. Other measurements are performed on the input data (half-family or photon), such as the depth-of-interaction (DOI) on the incident photon. DOI measurements solve the problem of identifying the affected crystal when the incident photon arrives at an oblique angle instead of perpendicularly to the face of the crystal. The 3D-Flow processor can utilize several DOI measurement techniques known well to those of ordinary skill in the art, such as may be found in "A Novel APD-based detector module for multi-modality PET/SPECT/CT scanners," by Saoudi, A., and Lecomte, R., IEEE Conf. Rec. Nucl. Sci. Symp. and Med. Imag., pp. 1089–1093, 1998; "Effect of Detector Scatter on Decoding Accuracy of a DOI Detector," by Miyaoka, R. S., et al., IEEE Conf. rec. of the Nucl. Sci. Symp. and Med. Imag. M3–34, Seattle, Oct. 24–30, 1999; and "Development of a 64-channel PET detector module with depth of interaction measurement," by Huber, J., et al., IEEE presentation at the Nucl. Sci. Symp. and Med. Imag., M4–6, Seattle, Oct. 24–30, 1999, for correcting the effect commonly referred to as "parallax error."

7. Finally, the half-family is reunited (the total energy of the photon is calculated), all measurements are performed, and results are sent to the channel for its trip to the exit (See in FIG. 2A the object r4 in the fourth station from the top, which is the result of the input data No. 4).

Only some of the above processing is carried on in the prior art PET devices. The most important task of rebuilding the energy of the incident photon (equivalent to reuniting a half-family) is not performed. On the contrary, prior art PET techniques add analog signals before checking whether the signals belong to the same incident photon; this is equivalent to grouping father and children before checking if they belong to the same half-family.

Adding several analog signals before checking whether the signals belong to the same incident photon, as is done in prior art PET, turns out to be very counterproductive at the next electronic stage because the analog signal (which is the sum of several signals) cannot be separated into its original components and the information on the single photons that is needed for several subsequent calculations is lost forever.

In the most advanced prior art PET devices, the electronics cannot complete the processing before the arrival of another data set; therefore, consequently, dead time is introduced and photons are lost.

The conclusion is that the limitation of the electronics of the prior art PET (front-end and coincidence detection, described later) prevents it from detecting many photons, and the overall performance of the best prior art PET device detects about two photons in time coincidence out of 10,000 emitted by the radioactive source. This should be compared to 1,000 photons out of 10,000 captured by the 3D-CBS, with its improved electronics and extended axial FOV. In addition, of the two out of 10,000 photons in coincidence captured by prior art PET devices, many will be discarded by subsequent processing, or they will not carry accurate information.

Conversely, the advantage of the 3D-Flow architecture of the 3D-CBS is a result of using of several layers of stations (processors) with the data flow controlled by "bypass switches" (or multiplexer) allowing more than, for example, 50 nanoseconds to weigh the subject, to take the picture, to exchange them with the neighbors, to calculate the local maxima, the center of gravity, etc. The use of 50 ns herein is not intended as a limitation of the scope of the invention; it is merely an exemplary value. The 3D-Flow system can be designed to sustain a sampling rate higher than the faster crystal detector currently employed in the industry. Five layers of stations (or processors at the same level) allow 250 nanoseconds in each station to perform all of the above calculations. In the event this processing time is not sufficient, more layers are added.

The bypass switches will provide good synchronization of input data and output results at each station (or processor) by simply taking one data packet for its station and passing four of them along.

Using the scheme depicted in FIG. 2A, it is possible to follow the path of a data packet of photon (i3) through the entire system. At time 5t shown in FIG. 2B, the data packet of photon i3 enters the channel at the top of FIG. 2A. If it finds a busy station (processor) on the right, it rests for one cycle on the platform (or register, shown in FIG. 2C as a rectangle next to the bypass switch).

During the next cycle, 6t of the table in FIG. 2B, this data packet of photon (i3) advances to the next station. If this station is also busy, then it will rest on the next platform, and so on until it finds a free station.

When the data packet of photon (i3) finds a free station (at time 7t in FIG. 2B), it enters the station and stays there for five cycles for processing. After the data packet of photon r3 (which contains the results of the processing performed on i3) leaves the station and goes to the platform on the left, adjacent to the station (at time 12t), another data packet of photon (i8) enters the station from the upper left platform. The result from photon (r3) cannot go straight to the exit but can advance only one platform at a time until it reaches the exit.

In summary, the 3D-Flow sequentially implemented parallel-processing system is synchronous; it has a fixed number of steps and a fixed sampling rate, the data flows in an orderly fashion from input to output according to the time clock, and there is no congestion in the flow. The sequence is as follows:

synchronously receive a data packet from the input of the system synchronously send out a data packet from the output of the system with a fixed time latency from when it was received by the system and with a tag identifying the result as either a non-data, a good CT photon, a good PET photon, or a Compton scatter photon, etc.

process each data packet fully, with information exchange with neighbors, by a 3D-Flow processor in one layer of the system, regardless of whether or not it contains relevant data; no data packet is skipped or lost. The 3D-Flow system is dimensioned with the correct number of layers needed to fulfill the requirements of executing the real-time algorithm in full (a fixed maximum number of steps) on each data packet and of sustaining the maximum input data rate. There is always a free processor waiting to receive a data packet. If a processor finds no meaningful results and terminates its process in fewer steps, it waits its turn (because it is a synchronous system) before it sends out the result and fetches a new data packet at the input. If either the input data rate or the complexity of the algorithm increases, one or more layers are added to satisfy the requirement of zero dead-time. (See FIG. 2A).

The next phase is to reunite husbands and wives (the two half-families reunited in description above) from distant locations, or find the back-to-back photons in time coincidence. The measurements performed during phase I have reunited the half-families (each parent with some children), creating good candidates for the final entire family reunion. The result of the previous process is that, at most, four new fathers (or mothers) are found every 50 seconds over the 1,792 channels. It is initially assumed at the beginning of this analogy of the need to reunite at the reunion center only 12% of 17 families (17 fathers+17 mothers) separated every 50 seconds 3 which is equivalent to about four photons (two photons back-to-back per event) arriving at the coincidence circuit on average, for example, every 50 nanoseconds (which corresponds to a radiation activity of about 9 mCi administered to the patient). Six comparisons every 50 nanoseconds, for example, are necessary in order to find all possible matches among the four photons. A coincidence circuit with the capabilities of performing six comparisons every 50 ns (or 120 million comparisons per second) can handle a radioactivity of about 9 mCi of FDG which is far more than the expected 0.3 mCi of FDG estimated to be required by the 3D-CBS for cancer screening. The implementation of a coincidence circuit that will perform more comparisons per second will not be a challenge even if higher doses of radioisotopes with shorter half-life, such as $^{15}$O-water or $^{82}$R rubidium are used. The calculation of the rate of the photons that hit the detector is as follows: 9 mCi ×3.7×10 7=333×10 6 disintegrations per second (or about 17 families separated every 50 seconds in the family reunion paradigm, which, recall, has an event rate one billion times slower).

The approach used in prior art PET devices in the final reunion is that the fathers and mothers do not move from the location where they are and each location interrogates about half of all the other locations explaining that it is not necessary to test Lines of Response—LOR—which do not pass through the patient's body in order to find out whether there is a companion in that location.

Because, as mentioned elsewhere herein, there are about 2,000 locations (electronic channels) in the system, the total number of comparisons that must be performed in order to find the companion will be enormous. For instance, for a PET with 1,792 channels, the number of comparisons 28 necessary would be: (1,792*1,791)/4=802,368 comparisons every 50 ns; that is equivalent to sixteen trillion comparisons/second (The division by 4 in the formula is required because approximately half the LORs do not pass through the patient's body). Although in our human analogy, family events are one billion times slower, it would still require sixteen thousand checks of matching families per second.

In order to avoid making that many comparisons per second, manufacturers of prior art PET have reduced the number of locations (electronic channels). This has several drawbacks, such as increasing dead-time, reducing resolution, etc. For example, with a reduction to 56 channels, the number of comparisons in prior art PETs is still (56*55)/4=770 comparisons every 250 ns, or equivalent to about 3 billion comparisons/second, which are performed in seven ASICs in the current GE PET as taught by Mertens et al. in U.S. Pat. No. 5,241,181 entitled "Coincidence detector for a PET scanner" incorporated by reference herein in its entirety.

The approach used in the proposed 3D-CBS greatly simplifies the circuit and requires only 120 million comparisons per second as discussed in the present invention in co-pending patent application 10/296,532 (and as described in more detail in Section 13.4.14 and shown in detail in FIG. 13–22 of Modular VME. This efficiency is equivalent to that of the PET with 1,792 channels, which, as noted above, would require instead sixteen trillion comparisons per second.

Again, using the family paradigm, the approach can be explained as follows: the husbands and wives should move from their location to the reunion center. At that location an average of four groups of parents with their children arrive every 50 seconds (when an original family separation rate of 17 every 50 seconds is assumed); thus, in order to make all possible combinations among four elements and avoid accumulation in the room, six comparisons every 50 seconds are necessary. This would still be manageable in the world of the family reunion, only 7.2 comparisons per minute being required instead of sixteen thousand comparisons per second with the prior art PET approach, and with the 3D-CBS it would also be manageable in the world of photons requiring only 120 million comparisons per second.

As mentioned above, the advantages of the presently described invention are partly a result of how existing technology is coupled with the newly described electronics of the 3D-Flow system and partly due to the 3D-Flow system itself. These include increased input bandwidth of the electronics with less radioactive isotope in the patient, greater field of view (FOV) and more accurate identification of most photons.

In accordance with one exemplary embodiment of the present invention, the 3D-CBS can be built using off-the-shelf detector components and the 3D-Flow processor implemented in FPGA. Such combination provides a system input bandwidth of the electronics of 10 billion events per second (instead of the current maximum 10 million events per second). Thus, the goal of reducing the radiation dose to a level lower than 100 mrem/yr is achieved. In accordance with one exemplary embodiment of the present invention, the 3D-Flow processor used in the 3D-CBS device is implemented in ASIC, thereby further reducing the radiation dose with the use of the 3D-Flow (which can provide an input bandwidth higher than 36 billion events per second) will further lower the radiation to the patient and will provide better images.

Figure 3:
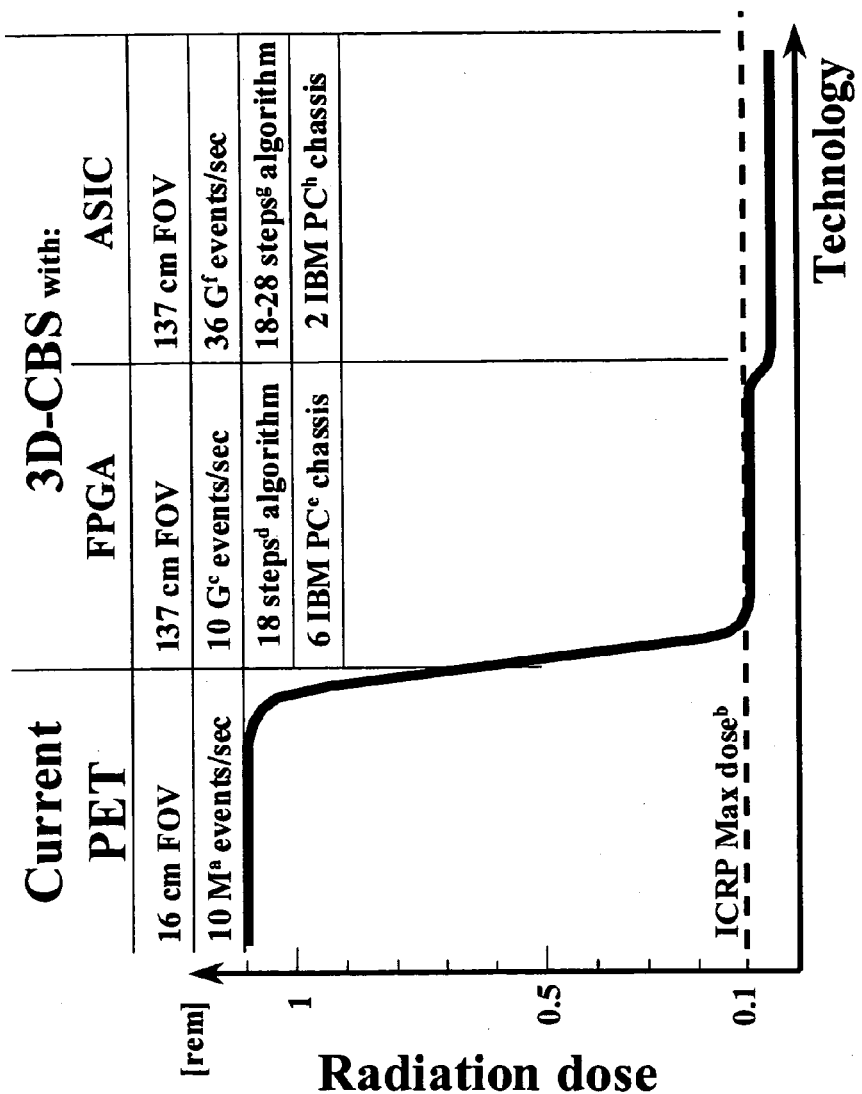
FIG. 3 is a diagrammatic roadmap of the construction of the 3D-CBS with different technologies in accordance with exemplary embodiments of the present invention.

FIG. 3 is a chart of the correspondence between radiation dosage and PET technology. Essentially the chart depicts a diagrammatic roadmap of the construction of the 3D-CBS with different technologies in accordance with exemplary embodiments of the present invention. The ""Current PET" column describes salient attributes of the prior art PET device. Accordingly, an 1100 mrem dosage of radioactive isotope yields an input bandwidth of approximately 10 million events/sec. for a 16 cm detector field of view (FOV), according to "The Changing of Positron Imaging System. Clinical Positron Imaging," vol. 1(1):31045, 1998 Phelps, M. E., et al. Thus, the prior art PET devices operate well above the recommended limit of 100 mrem/yr (average over five years) for exposure to ionizing radiation for the general population set by the ICRP and the NCRP (ICRP Publication 60, Annuals of the ICRP 21, pp. 25; 1991 and Ordonnance sur la radioprotection (OraP) Le conseil federal suisse. 19 Dec. 2000). Thus, one PET (or CT) procedure using prior art technology exposes a patient 10 to 20 times the allowable dosage.

The "3D-CBS" column is subdivided into two subheadings, 3D-CBS implemented in Field Programmable Gate Array (FPGA) (programmable logic chip embodiments) and 3D-CBS implemented in Application Specific Integrated Circuit (ASIC) (application/design-specific chip embodiments). In comparison with the prior art PET, the 3D-CBS with FPGA realizes an input bandwidth of 10 billion events/sec through a detector that has a FOV about 137 cm long (calculated as 6 MHz input bandwidth of each 3D-Flow processor times 1792 electronic channels). The capability to execute an 18-step real-time algorithm (during each step, the 3D-Flow processor can execute up to 26 operations simultaneously) allows for accurately identifying the characteristics of the interaction between the incident photon and the detector. The 3D-CBS with FPGA embodiment is configured six IBM PC chassis, five IBM PC chassis contains 19 Data Acquisition (DAQ) boards each, and one chassis with 17 DAQ boards. Each DAQ board is equipped with 16 channels with five sequentially implemented parallel-processing stages, implemented on 25 FPGAs. Each FPGA contains the functionality of 4×3D-Flow processors. Notice that radioactive dosage requirement for this embodiment is reduced to approximately 100 mrem from the 1100 mrem required by the prior art PET.

Finally, with regard to the 3D-CBS with ASIC embodiment, notice that while the FOV remains constant at about 137 cm from the FPGA embodiment, the input bandwidth increased to 36 billion events/sec from 10 billion of the previous embodiment. The bandwidth is calculated as 20 MHz input bandwidth of each 3D-Flow processor, times 1792 electronic channels. The ASIC embodiment enables the execution of a more sophisticated (longer than 18 steps) real-time algorithm which allows capturing more photons and improving the quality of the images. The more powerful algorithms are possible using application specific integrated circuit even though only two IBM PC chassis are employed, each containing 14 DAQ boards equipped with 64 channels on 25 ASICs, each with 16×3D-Flow processors. Consequently, the radioactive dosage body burden to a patient for this embodiment is reduced by half from the previous embodiment and far below the 100 mrem upper dosage threshold set by the ICRP.

FIGS. 4A–4D are diagrammatical comparisons of the relationship between the increasing FOV in Line of Response (LOR) in accordance with exemplary embodiments of the present invention. A PET with an axial FOV that is twice as long as the short FOV of the prior art PET can detect four times the number of photons in time coincidence from an organ emitting photons from the center of FOV. FIG. 4A and FIG. 4B and assume the detector has only three rings of detector elements. Only the LOR connecting opposite sets of detectors within the three rings are considered instead of all possible LORs passing through the patient's body. The top detector elements are elements A, B, C, and the bottom detector elements are depicted in the figure as elements D, E, F. For a linear source at the center of the FOV emitting pairs of photons in time coincidence in opposite directions, one could only capture three possible combinations AD, BE, and CF (See FIG. 4A) when SEPTA are used (septa are lead rings between the ring-detectors that prevent photons arriving with an angle from hitting the detector). Thus, FIG. 4A depicts the prior art PET devices with short FOV and further LOR limiting septa.

For the purpose of understanding how the capturing of photons is greater than doubled when the FOV is doubled, assume that the representation of the detector is simplified as shown in FIG. 4B, depicting a prior art PET device with the same short FOV as in FIG. 4A, but the number of photons captured increases from 3 to 9 when the SEPTA are removed. In the absence of SEPTA lead rings, there are nine possible combinations of pairs of photons: AD, AE, AF, BD, BE, BF, CD, CE, CF which can be captured.

FIG. 4C depicts the effect of doubling the axial FOV has on LOR. Doubling the FOV, thereby doubling the number of detector element rings, increases the Lines of Response four times over prior art PET devices with half the number of rings (or 12 times if compared to 2-D mode, shown in FIG. 4A). If the FOV is doubled and with new top detector elements G, H, L, and the new bottom detector elements M, N, P, then 36 combinations of pairs of photons emitted in opposite directions from a linear source in the center of the FOV are captured. The possible pairs for which a LOR could be drawn are: AD, AE, AF, BD, BE, BF, CD, CE, CF, plus the new GM, GN, GP, HM, HN, HP, LM, LN, LP, plus the combination of old top and new bottom AM, AN, AP, BM, BN, BP, CM, CN, CP, plus the combination of the new top and the old bottom GD, GE, GF, HD, HE, HF, LD, LE, LF.

Finally the LOR algorithm described above is infinitely extendable, for instance if the FOV is increased three times from that depicted in FIG. 4B, the number of pairs of photons that can be captured increases nine times (or 27 times if compared to the current use of the PET in 2-D shown in FIG. 4A). If the FOV is increased four times from that depicted in FIG. 4B, the number of pairs of photons that can be captured increases sixteen times (or 48 times if compared to the current use of the PET in 2-D shown in FIG. 4A).

Considering that most of the PET (even the most advanced) available currently in hospitals use a 2-D mode for the torso, where only the combinations AD, BF, and CF are detected, the difference between the prior art PET and the 3D-CBS when the FOV is doubled, is from 3 to 36 (or 12 times). If the FOV of the prior art PET is tripled from 16 cm to 48 cm, then the difference in captured pairs of photons will increase 27 times when using the 3D-CBS approach.

Cost of the 3D-CBS device is reduced, or kept at least to a minimum, through the use of low cost detector crystals. One type of scintillator crystal known for its cost effectiveness is the bismuth germanate (BGO) crystal. An even lower cost crystal is the sodium iodate (NaI) crystal; however, the disadvantages associated with NaI crystals have discouraged a large segment of the PET industry from using other more expensive crystal detectors, as mentioned elsewhere above. NaI crystals are less dense, and have less "stopping power" of the 511 keV photons than BGO crystals. BGO is more rugged, and allows for higher detection efficiency. Additionally, BGO is not count-rate limited, thus practitioners are encouraged to inject even larger dosages of isotopes in their patients because it has been surmised that the BGO can detect more counts and more counts result in clearer scans and sharper images. In fact, some estimates place BGO crystal usage at almost ten time that of NaI. Although the NaI crystal may have lower stopping power than the BGO, it provides a stronger signal.

Therefore, in accordance with another exemplary embodiment of the present invention, an improvement in the PET spatial resolution may be achieved by means of a more accurate measurement of the depth of interaction (DOI) using either low cost crystals such as BGO, or the NaI crystal which has even a lower cost. The photon's stopping power of the NaI crystal is increased by fabricating a thicker NaI detector in proportion to a comparable BGO detector, with a stronger signal. With a renewed interest in NaI detectors, there is a likelihood that NaI crystals will be grown ever larger, in fact, it is technologically possible to build a single barrel to cover the entire surface of the patient's body. Although, cost-efficiency criteria will most probably dictate an optimal segmentation and separation of the crystal that will cover most, but not all, of the patient's body.

Figure 5A:
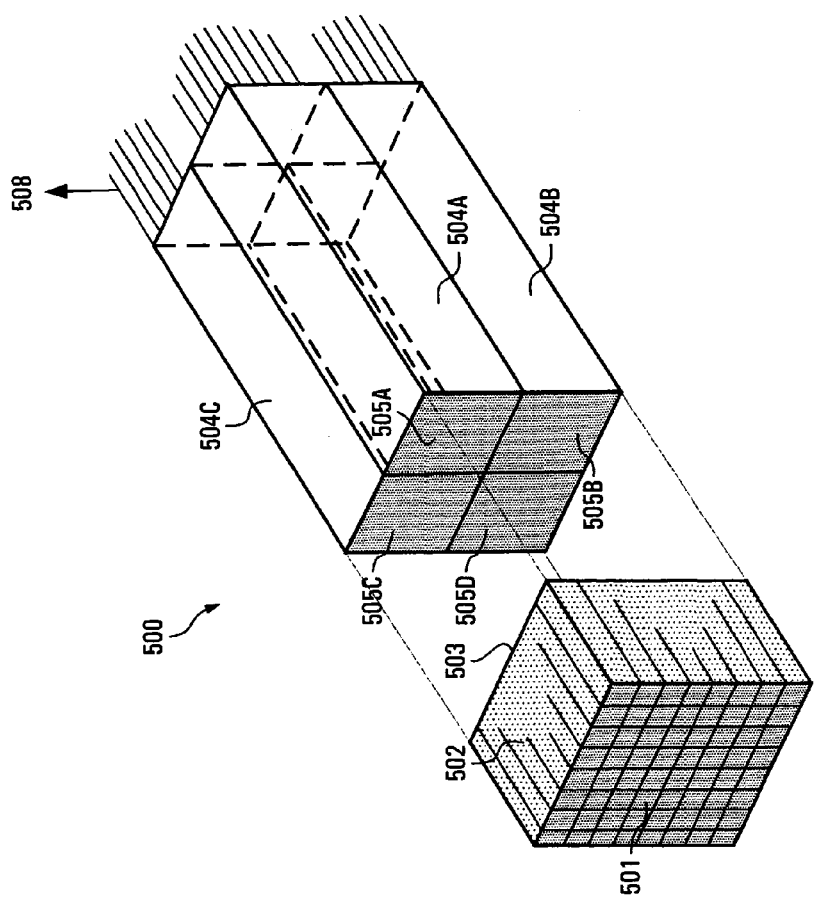
FIGS. 5A–5D depict a scintillation detector assembly as is well known in the prior art.
Figure 5D:
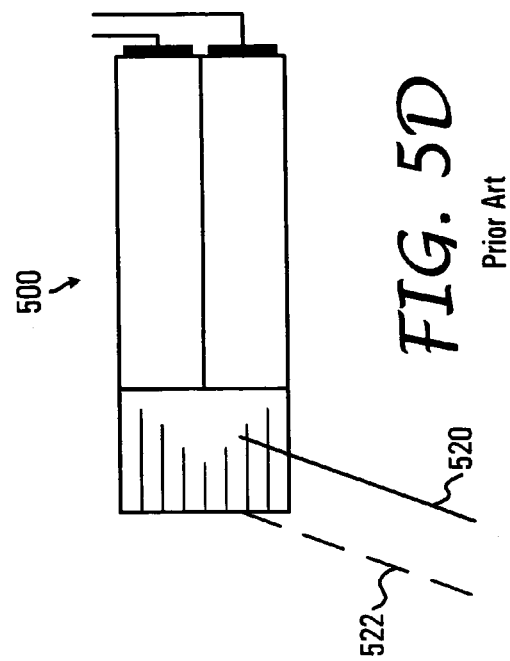

Measuring the DOI is important for correcting the parallax error. Parallax is the error that results from assuming that photons strike the detector at 90 degrees to its face. A better understanding of the parallax problem may be realized through a discussion of the prior art PET photon detector assemblies. With regard to FIGS. 5A–5D, a scintillation detector assembly is depicted as is well known in the prior art. FIG. 5A is an oblique view of a typical photomultiplier (PMT) module employed by, for example, prior art PET devices. Prior art assembly 500 utilizes a block detector design concept in which single crystal 502 is optically coupled to a 2×2 block (or module) of transducers 504A–504D.

Crystal 502 might be any type which interacts with a photon to produce a scintillation, or rapid flash of light, in the interior lattice structure of the crystal. However, recently prior art PET manufacturers have moved away from less efficient and cheaper crystal, focusing instead on more expensive crystals in an effort to increase the detector's efficiency. Notice that crystal 502 has interior face 501 which faces the patient on the interior of the barrel, exterior face 503 which is optically coupled to interior face 505 of the transducer. Notice also that prior art crystal 502 has been cut or slit into smaller crystals. The purpose of the cut (slits) between small crystals (pixels) is to reduce the number of photomultipliers affected by the light generated by an event (or interaction between the incident photon and the crystal). The length of these cuts which separates two crystals has to be determined experimentally and is different from crystal to crystal. Crystal 502 (coupled to prior art PMT module 504) is typically subdivided into an 8×8 block of variable length slits. The 8×8 block does not share light well with adjacent 8×8 crystal blocks associated with neighboring detector module assemblies. In general, the variable length slits allow only the PMTs in the module assembly that are coupled to a crystal receive light from that crystal. Moreover, edge and corner subdivisions of each prior art 8×8 crystal block contribute only a small signal compared to the contribution of the inner subdivisions of the crystal making the identification of photon events more difficult, and lowering the overall efficiency for the PET. Furthermore, if a photon strikes the boundary edge between adjacent 2×2 PMT modules (between the edge and/or corner subdivisions of two 8×8 crystal blocks), neither PMT may receive sufficient energy to recognize the strike as a photon and the photon is lost, further reducing the efficiency of capturing photons for the prior art PET device.

Transducers 504A–504D may be Photomultipliers (PMTs), Avalanche Photodiodes (APDs) or some other type of light emitting diode; however, each transducer-detector combination will have a signal output (a channel) for outputting the amplified signal to the processing electronics. Those of ordinary skill in the art will readily understand that a PMT is typically described as having an amplification section for amplifying the photon's energy and a sensor for receiving the amplified energy and converting it to an electrical signal.

Figure 5B:
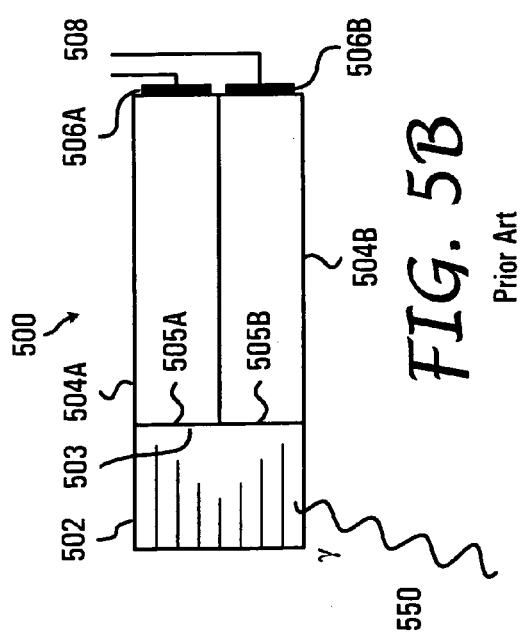
Figure 5C:
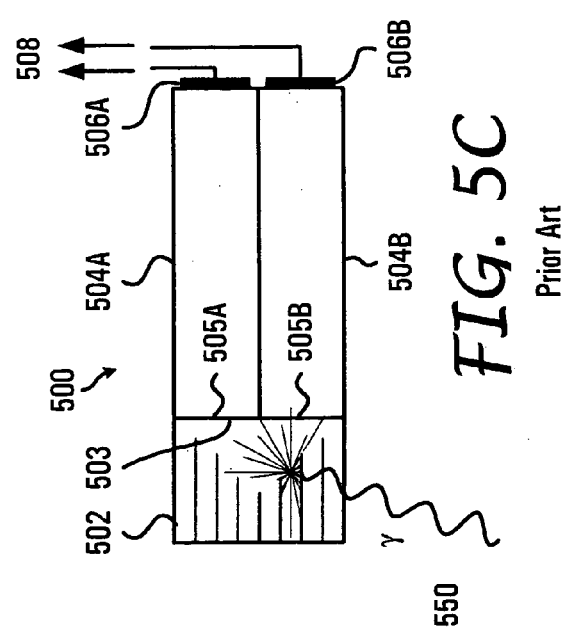

With regard to the parallax effect, notice from FIG. 5B that incident photon γ 550 is approaching crystal 502 at an oblique penetration (instead of being perpendicular) to the face of the crystal looking toward the emitting source. Only transducers 504A and 504B are depicted for simplicity. When a photon enters the crystal at 90 degrees, its X-Y position can be easily calculated from the detectors which perceive the scintillation effect in the crystal, the XY position through a centroid calculation. An exemplary centroid calculation for 2×2 detector array(detectors A, B, C and D) is:

$$X_m = \frac{(A+B)-(C+D)}{A+B+C+D} \quad Y_m = \frac{(B+D)-(A+C)}{A+B+C+D}$$

(A better calculation for determining A, is the ratio of the sum of the energies of all sensors at the west of the central element, divided by the sum of all sensors at the east of the central element ($\Delta_x = \Sigma E_W / \Sigma E_E$). Similarly, for the calculation of $\Delta_y$, the ratio of the sum of the energies of all sensors at the north of the central element, divided by the sum of all sensors at the south of the central element ($\Delta_y = \Sigma E_N / \Sigma E_{S'}$)).

The depth at which the photon interacts with the crystal is unimportant in this case where the photon penetrates the crystal perpendicular to the face because it will interact somewhere along a line oriented in the Z direction formed by the intersection of an X plane and a Y plane, i.e. the LOR is found perpendicular to the X-Y planes. This presumes that all lines of response between coincidental pairs of detectors intersect the center point of the barrel which is very imprecise. In practice, once the detector elements 506A and 506B receive an optical signal, an analog signal is produced at output 508 and sent to the PET electronics (the coincidence board(s)). Generally, the PET electronics which compares all of the possible LOR for coincidences, even those connecting two detectors that did not receive a hit. When a coincidence is determined, the resulting LOR is used for generating the image. However, the parallax effect shifts the placement of the endpoints of the LOR along the Z axis to some default depth, such as the mid point or face of the crystal. The error is apparent on FIG. 5D, where both LOR 520 and LOR 522 are correctly spatially positioned on the X-Y plane of detector 502, but only LOR 520 is at the proper depth. Often, if a DOI calculation is not performed, the LOR is found by correspondence using a default depth, e.g. midway down the detector, on its face, etc. The results of not calculating a DOI are graphically illustrated in FIG. 5D by the separation between LOR 520 and LOR 522.

Therefore, the parallax error resulting from incident photons with angles different from a 90-degree measurement is corrected by determining an accurate interaction depth, and using the depth to properly place the LOR. DOI is determined by comparing the photon's energy, as captured by two different sensors, and relating the difference to the interaction depth of the photon in the crystal. Best results are obtained when the two sensors are positioned to make maximized variations in energy based on the depth of interaction. One sensor should offset depth with respect to the Z axis. In accordance with an exemplary embodiment of the present invention, the measurement of the depth of interaction to correct the parallax error of incident photons with angles different from 90 degrees can be performed by using two sensors, for instance, Photomultipliers (PMT) and/or Avalanche Photodiodes (APD) on either side of the detector crystal, one being positioned internal to the barrel and the other being positioned external to the barrel. For instance, by using an array of photomultipliers internally and externally and then interpolating the signals received by the two sensors.

Figure 6:
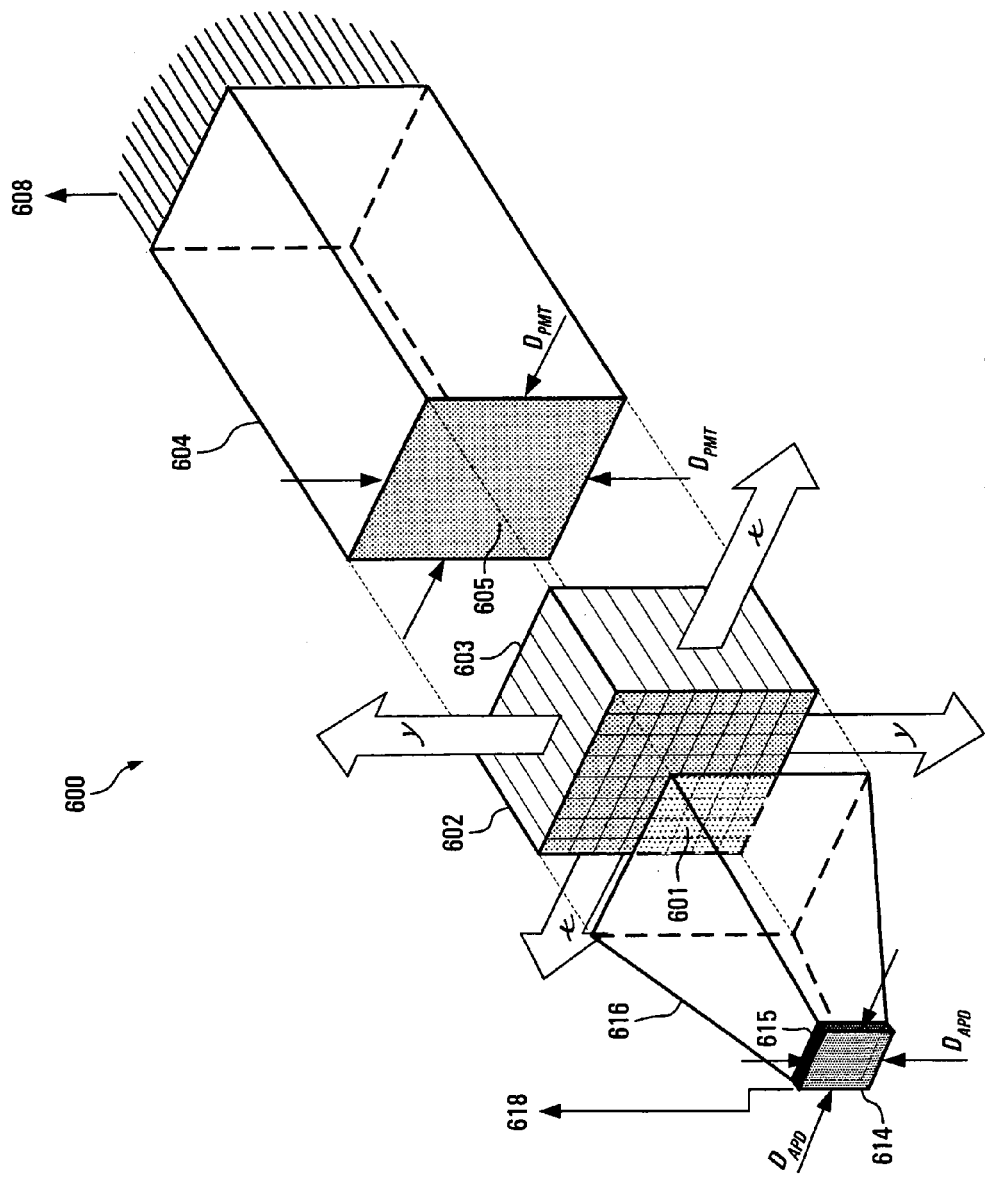
FIG. 6 is a diagram of a detector assembly having two sensors for measuring the depth of interaction to correct the parallax error in accordance with an exemplary embodiment of the present invention.

FIG. 6 is a diagram of a detector assembly having two sensors (or transducers) for accurately measuring the depth of interaction of a photon in the crystal in order to correct the parallax error in accordance with an exemplary embodiment of the present invention. Detector assembly 600 generally comprises crystal 602 having an interior face 601 and an exterior face 603, which is optically coupled directly to exterior face 605 (or window) of external transducer 604 which is a sensor (e.g., an APD or photomultiplier) on the opposite side of the detector from where the radioactive source is located. Interior face 601 of crystal 602 is connected to light guide 616. The interior opening of light guide 616 is coupled to interior face 615 (or window) of internal transducer 614, which is a thin sensor (e.g., an APD) in front of the detector (the side where the radioactive source is located and the photon is arriving to hit the detector). In accordance with an exemplary embodiment of the present invention, detector assembly 600 employs Photodiodes or APD as internal transducer 614, rather than a PMT, to improve efficiency. The semiconductor material comprising a photodiode or APD will not absorb or scatter many photons that penetrate the face of the crystal because it is comprised of an extremely thin material of only a few hundred microns.

Here, it should be also noted that in contrast with prior art detector assemblies configured for DOI calculations, the 3D-CBS processor stack uses the signal outputs from the exterior PMTs for the vast majority of the data to be used for image generation. As mentioned above, the present system is hundreds, if not thousands, of time more efficient than the prior art PET device using only the photomultipliers. Therefore, while the 3D-CBS architecture could easily accommodate a complex interior sensor arrangement, such as an array of interior sensors, there is simply no need to expend the resources on developing interior sensors and signal channels that will be used for only one purpose, that is to be compared to the exterior signals for an interaction depth. To that end, the present interior sensors are chosen and configured with cost effectiveness as a primary intent. The results of the choices on the detector configuration are strikingly different than any interior sensor arrangement hereto. For instance, one means for achieving cost effectiveness is by reducing the coverage area of the APD.

Notice from FIG. 6 that, although the detector 602 has approximately the same area as the face of PMT 604, the coverage area of APD is much smaller than the face of crystal 604. For the purposes of the present invention, this makes absolute perfect logic. The faces of crystal detector 602 and PMT 604 should be comparable for better optical coupling and lowering the risk of missing an event. The requirements for coupling APD 614 are much less stringent. In fact, since what is sought from APD is a reasonably accurate signal, the diode utilizes optical guide 616 to collect and channel the scintillation from crystal 602. In stark contrast with prior art DOI schemes, it is simply not necessary to use the interior sensor for anything other than collecting an optical signal to be compared with the exterior channel signals.

In accordance with an exemplary embodiment of the present invention, the area of window 605 for external transducer 604 ($D_{pmT}$) is greater than that of window 615 for internal transducer 614. As depicted in the figure, the diameter of window 605 ($D_{PMT}$) is greater than the diameter of window 615 ($D_{APD}$), $D_{PMT} >> D_{APD}$, and therefore, the surface area $(D_{PMT})^2$ of window 605 of external transducer 604 is proportionally larger than the surface area $(D_{APD})^2$ of window 615 of internal transducer 614. Keeping the surface area of internal transducer 614 smaller than that of external transducer 604 has two advantages. First, both APDs and photodiodes typically cost much more than PMTs. Therefore, reducing the size of the APD reduces the cost of employing APDs. It should also be noted that presently, in addition to being more costly, Photodiodes and APDs also have a lower gain; however, it is expected that those deficiencies will probably abate somewhat as the convenience of using Photodiodes or APD internally and externally becomes more apparent. Second, because the detector obscures only a portion of the face of crystal 602, not every photon penetrating from the crystal's face will pass through detector 614.

The operation of detector assembly 600 shown in FIG. 6 will now be described with regard accurately determining DOI for reducing the parallax error. In the following discussion, transducer 604 is optionally referred to as a PMT, while transducer 614 is optionally referred to as an APD; however, these references are not intended to limit the scope of present invention.

The light captured by the two transducers is proportional to the energy of the incident photon and to the distance where the photon was absorbed by the crystal with respect to the location of the two transducers. Light captured by the two transducers is converted into electrical signals 608 and 618. The two signals are then converted into digital form and sent to the 3D-Flow processor, which computes the interpolation of the distance from the two sensors, which is proportional to the location where the photon hit the detector. This measurement more accurately determines the location where the photon hit the crystal (the depth of interaction), rather than assuming the photon strikes that crystal face at 90° and traverses the crystal along its optical axis. Parallax error due to poor DOI assumptions is therefore eliminated and spatial resolution is correspondingly improved.

Figure 7C:
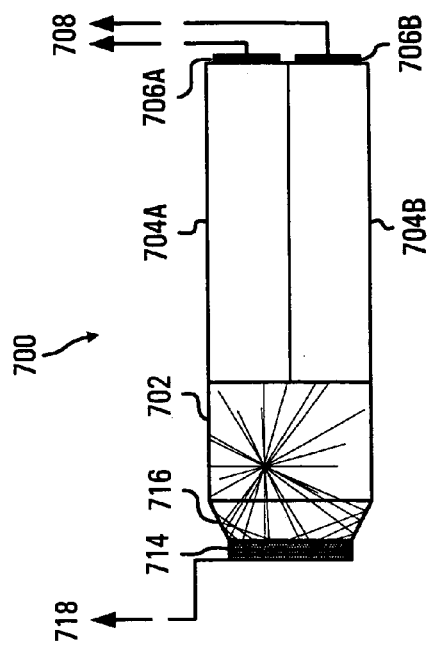
FIGS. 7A–7C depict a scintillation detector assemblies in accordance with exemplary embodiments of the present invention.
Figure 7A:
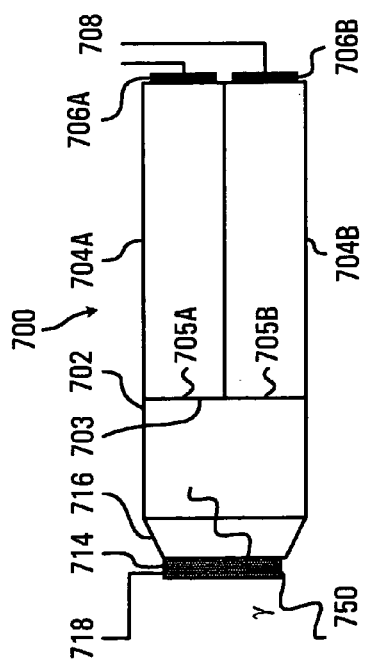
Figure 7B:
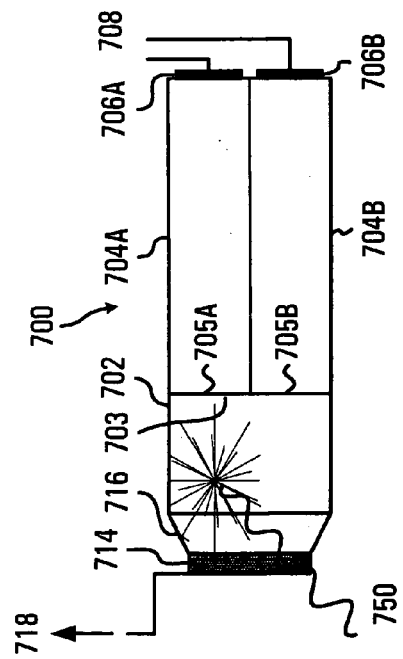

Here, it should be understood that the present invention for improving DOI determinations is extremely adaptable. The detector assembly can be arranged in several configurations for use in a PET. For example, and as generally depicted in FIG. 6, detector assembly 600 may have a 1:1 correspondence between the number interior transducers 614 and exterior transducers 615. As mentioned above, exterior transducer 615 may have a smaller surface area than that of interior transducer 614. In accordance with another exemplary embodiment of the present invention, the correspondence between the number of interior transducers 614 and exterior transducers 615 may instead be 1:M (one to many), as depicted in FIGS. 7A–7C below. M is defined as an N×N grouping of PMTs having their interior windows coupled to the exterior opening of the light guide (2×2, 3×3, 4×4, 5×5 and so on). DOI determinations are made in exactly the same manner as described above, between the interior transducer and local maxima. The local maxima is defined as the head of a cluster of PMTs for an impact (the cluster of PMTs is NOT the same N×N grouping of PMTs coupled to the light guide but may instead extend beyond that group and be coupled to other light guides). Finding a local maxima and an XY position of an interaction in a boundary-free cluster of PMTs is disclosed in U.S. patent application Ser. No. 10/706,824, U.S. patent application Ser. No. 09/506,207; U.S. patent application Ser. No. 10/185,904; and U.S. patent application Ser. No. 10/296,532 identified above and are each incorporated by reference herein in their entireties.

Regardless of whether the detector assembly is arranged in 1:1 interior transducers 614 to exterior transducers 615 correspondence or a 1:M, crystal 602 may be configured in one of several shapes. The first being similar to that known in the prior art wherein the crystal is coupled to a single PMT, alternatively to a PMT module having four individual PMTs. Although FIG. 6, and others, depict the detector as having been segmented into small rectangular shapes, that depiction is not intended to limit the scope of the present invention. Despite the fact that the crystal detectors may be cut in small pieces, alternatively, and as stated above, the entire barrel can be fabricated from several sectors (two, four or eight arc segments). Still further, the barrel may be constructed as a single piece surrounding the entire body of the patient. In those cases, and with regard to a 1:1 transducer arrangement, the external opening of light guide 616 covers an area of crystal 602 proximate to, and equivalent in size to window 605. Alternatively, the external opening of light guide 616 covers an area of crystal 602 proximate to, and equivalent in size to multiple windows for multiple PMTs (see FIGS. 7A–7C below). Moreover, because the processors in each signal channel of the 3D-CBS processor stack share information with each of their neighbors, photons interacting with an edge or corner of crystal 602 are properly identified, thereby allowing the DOI determination to proceed as described.

Turning now to FIGS. 7A–7C, a scintillation detector assembly having a sensor on either end of the detector is depicted absorbing a photon in accordance with an exemplary embodiment of the present invention. Assembly 700 comprises crystal 702, amplifiers 704A and 704B and corresponding sensor/transducer 706A and 706B (generally referred to cumulatively as transducers). Here again, crystal 702 may be any known or heretofore unknown type of detector which interacts with a photon so as to produce a scintillation, or rapid flash of light, in the interior lattice structure of the crystal. Crystal 702 may be coupled to one or more optical amplifier/sensors which have a detector integrated therein. Also, as discussed with regard to FIG. 6, transducer 704 is depicted as a PMT, while transducer 714 is illustrated as an APD. Notice from FIG. 7B, however, that transducer 714 was the first to receive an optical signal from crystal 702, resulting in output electrical signal 718, while at a later time transducer 704 receives the optical signal from crystal 702, resulting in output electrical signal 708. It should be cautioned, however, that the order in which the optical signals are received and the timing are relatively unimportant. The present invention utilizes the energy levels, not the arrival times, at the respective sensors to determine the DOI of the photon in crystal detector 702. The depth of interaction, not the arrival times, is proportional to the respective signal strengths. In any case, once electrical signals 708 and 718 have been generated, they are passed to the 3D-CBS DOI electronics for integration and depth determination. To that end, optical guide 716 collect sand redirects the optical signal toward the active portion of APD 714 in an extremely cost effective manner.

Manufacturers of prior art PET devices often rely on highly efficient scintillator crystals for increasing PET efficiency which substantially increases the cost of the PET device. Therefore, the particular crystals are chosen to be relatively short (10 mm) to limit the cost associated with the crystal. Shorter crystals have the added benefit of minimizing parallax in the prior art PET because less of the crystal is exposed for a photon to penetrate at an oblique angle. Because the present invention enables a highly accurate DOI determination, the crystals selected can be longer to compensate for lower efficiency, and therefore cost substantially less than prior art PET devices. The longer crystal results in more photon stopping power and better overall efficiency for less cost than is typically achieved in the prior art. Moreover, because the DOI can be accurately determined, higher resolution images are possible even when using a lower cost, less efficient scintillator crystal, such as a bismuth germanate (BGO) crystal or a sodium iodate (NaI) crystal.

At present, the exterior sensors are PMTs for the reasons discussed above. However, correction of parallax errors from incident photons with angles different from 90 degrees can be performed by using two sensors (Photomultipliers or Avalanche Photodiodes APD) on both sides of the detector, one internal to the barrel and the other external to the barrel. For instance, by using an array of photomultipliers internally and externally and then interpolating the signals received by the two sensors. In accordance with one aspect of the present invention, using a Photodiodes or APD internally that will not absorb or scatter many photons will significantly improve efficiency of the system because of its small thickness of material of a few hundred of microns, and PMT externally. Photodiodes or APD will cost more than PMTs and have a lower gain; however, future technology advances will show that it will be convenience to use Photodiodes or APD internally and externally. Although many figures on this non-provisional patent show the symbol of the detector cut in a small rectangular shape, the idea described in this non-provisional patent is not limited to crystal detectors cut in small pieces, but, as stated above, the entire barrel can be made of several sectors, four sectors, two sectors or at the limit a barrel in a single piece surrounding the entire body of the patient. This detector can have sensors (PMT, APD, or photodiodes) internally or externally to the barrel.

Figure 8:
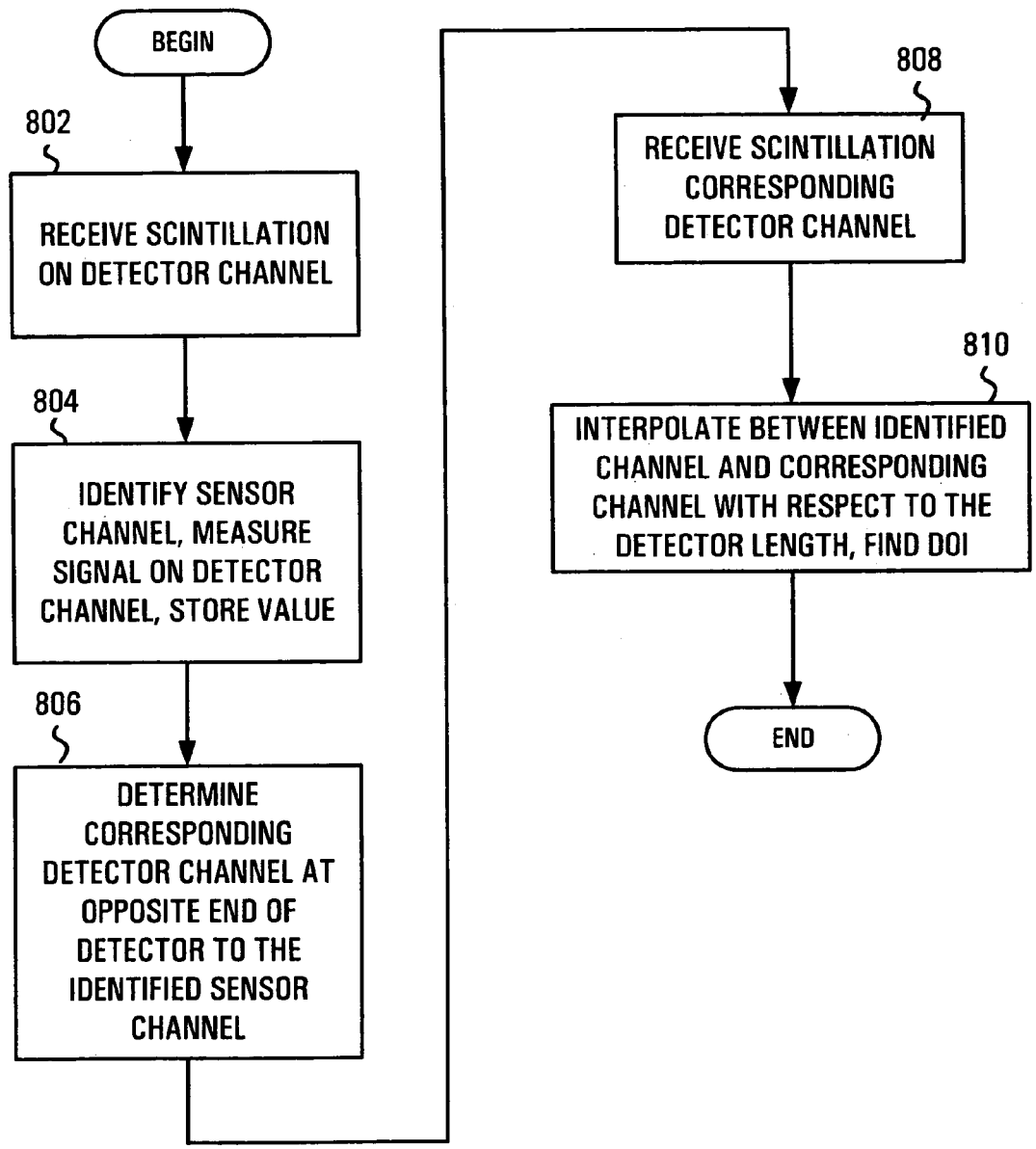
FIG. 8a is a flowchart of the process performed by the 3D-CBS system for determining DOI from the interior and exterior sensors on a crystal detector in accordance win an exemplary embodiment of the present invention.

FIG. 8 is a flowchart of the process performed by the 3D-CBS system for determining DOI from the interior and exterior sensors on a crystal detector in accordance with an exemplary embodiment of the present invention. The DOI process begins with any sensor receiving an optical signal generating the crystal 702 by a photon being decimated (step 802). Typically, the signal is in analog form from the sensors and should be converted to a digital signal prior to inputting to the DOI hardware. From the perspective of the DOI algorithm, it is unimportant whether interior sensor 714, receives the input prior to exterior sensor 504/506, or vice versa. However, because the orientation of the Z direction of the crystal is important, the sensor must be identified as being one of an interior channel or exterior channel sensor, and then the specific detector should be identified in some manner enabling the DOI hardware to look for signals on opposite and corresponding channels which correspond to the received channel signal for the detector (step 804).

What is intended is that the Z (perpendicular) depth of the interaction in the crystal be determined. Therefore, corresponding signal channels to be used by the DOI algorithm are taken, if possible, from interior and exterior sensors lying on the detector's Z axis. In other words, logic dictates that the optimal choices for a single corresponding pair of interior and exterior corresponding sensor pair are those having identical X-Y positions and vary only in the Z direction, i.e., the axial direction of the detector. However, as has been discussed repeatedly, the 3D-CBS processing architecture is extremely powerful and programmable to accommodate a variety of algorithms. Moreover, the majority of important signal information is derived from the exterior channels. Therefore, the interior channel signals are far less important, being used only as a basis for comparison with the exterior channels for calculating DOI and correcting parallax errors. Noise and transients can be filtered using the 3D-CBS and the DOI determined by interpolating signals from a multitude channels.

Once one channel signal has been received and digitized, the DOI processing hardware "watches" the channels associated with the corresponding sensors for an input. Normally, the signal arrives almost instantaneously with another, but the possibility exists that no signal will be forthcoming, and time out.

Upon receiving the channel signal from the corresponding sensor, it is also A/Ded and passed to the DOI hardware (step 810). Here again, the 3D-CBS architecture is a very powerful system and can easily process multiple channels from a sensor, such as an array of Photodiodes, APDs or PMTs, but given the single purpose of the interior channels, it is doubtful that the added expense could result in any better DOI values. Thus, the interior and exterior channel signals are interpolated toward a value that is indicative of the depth in the detector barrel where a photon was observed causing the scintillation. Using the depth measurement, the parallax error can be corrected using simple trigonometric functions and a more accurate placement of the LOR is determined.

Figures 9A, 9B:
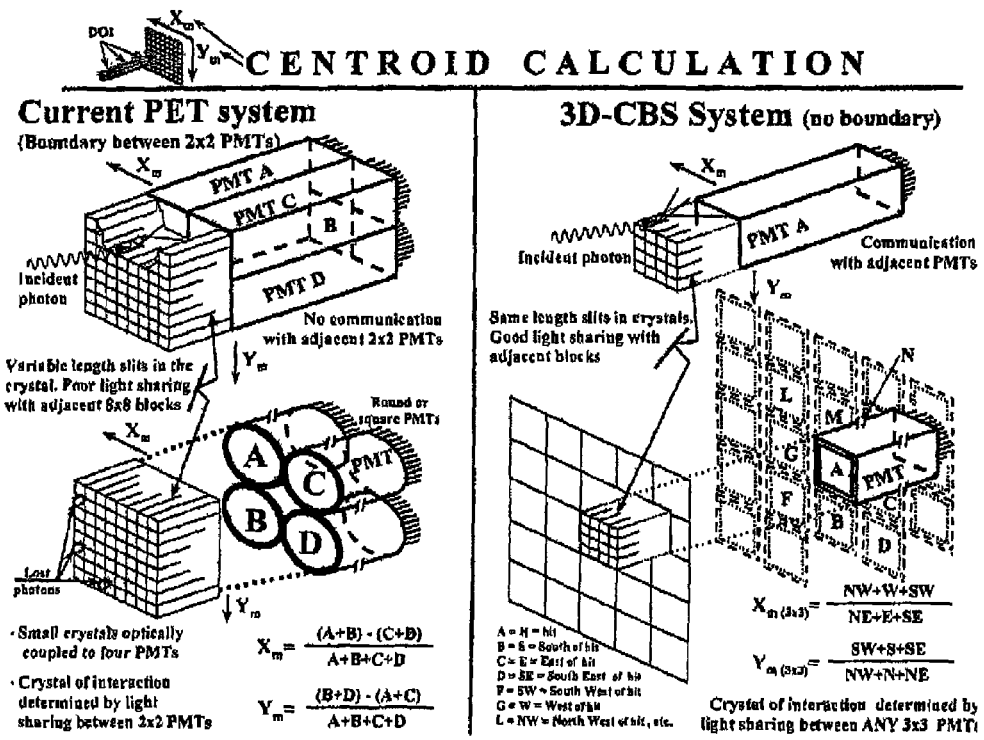
FIGS. 9A and 9B depict exemplary apparatus and methods for centroid calculation in a currently available PET system and in a system according to the present invention.

FIG. 9A shows a comparison of a detector assembly of a currently available PET system, which has a 2×2 array of PMTs (or module) detector boundary limitation compared with exemplary 3D-CBS assembly with crystals coupled to PMT (or APD) sensors which allows centroid calculation with no detector boundary limitations. The block detector of the current PET (FIG. 9A) consists of four 4 PMT tubes coupled to a set of crystals (64 crystals in the example of the figure). The variable lengths of the slits (made of reflecting material) in the crystal act like a light guide that allows more or less light sharing between the four PMTs. The long slits of reflecting material at the edges of the 8×8 crystal block allow minimal or no light sharing between adjacent 8×8 crystal blocks (or 2×2 PMT blocks). The identification of the crystal of interaction in the 2×2 PMT block is made through the Anger logic shown at the bottom of the figure. The crystals at the edges and corners of the 8×8 crystal block contributes a smaller signal compared to the inner crystals, making their identification more difficult. In contrast, the 3D-CBS assembly (FIG. 9B) solves these problems by permitting all crystals to have the same degree of light sharing with adjacent crystals with slits of equal length. As shown, the slits terminate within the crystal, which allows for sharing of the light with adjacent PMTs in the four directions with no boundaries. The interconnections in the North, East, West, and South directions of the electronic channels of the 3D-Flow system allow any PMT receiving the highest signal to be identified as the center of a 3×3 (or a 5×5) cluster which then rebuilds the total energy of the incident photon by summing all the adjacent signals and by calculating the centroid as shown at the bottom of the FIG. 9B.

The present invention will change the way health care is practiced. Preventive health care will receive a boost because, with this discovery, a safe, low-radiation preventive screening examination will be available. Prior art PET examinations require 1100 mrem of radiation, more than 10 times the exposure deemed acceptable in one year by the International Commission for Radiation Protection, and cannot be approved for preventive screening. The 3D-CBS, on the other hand, requires less than 100 mrem of radiation, well within the guidelines of the ICRP. Moreover, there will be a revolution in the way the images will be displayed. The image resulting from an examination with the 3D-CBS is three dimensional, visualizes the whole body at one time because data are recorded at the same time over the entire body, and has greatly increased definition. No more slices of the body, but real 3-D images of any organ of the body can be seen. There will be no more need to take several cancer screening examinations, but only a single, more efficient examination that will detect not only cancer, but also other diseases. Several current diagnostic devices, such as Single-Photon Computed Tomography (SPECT), gamma camera, etc. which capture only one out of 300,000 photons emitted, will become obsolete.

Just to mention a few consequences of this revolutionary discovery among those that will change the way medicine is practiced: There will be an impulse toward preventive medicine because this discovery opens up the possibility to perform non-invasive annual examinations at radiation doses accepted by the ICRP on asymptomatic people. This discovery will eliminate the current display of the body in slices and will making it possible to obtain real 3-D pictures of any organ in the body at the fused anatomical and molecular level because the data are acquired at the same time over the entire body. It will be an essential tool to develop and study the effects of new, experimental pharmacopeia. It will lower the cost of health care by combining in a single exam the examination of many organs, thus eliminating the need for several different, expensive (and sometimes invasive) procedures of screening for cancer such as mammogram, colonoscopy, etc.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A detector assembly for improved depth of interaction determinations comprising:
   a scintillator crystal for interacting with a photon from a photon source and creating a plurality of optical signals, said interaction occurring at an interaction site within said scintillator crystal and being characterized by an x-position, a y-position and a z-position, said scintillator crystal having a first end and a second end;
   at least one first transducer for receiving one of the plurality of optical signals from said scintillator crystal and converting the one of the plurality of optical signals to a first electrical signal, said first transducer having a first active area for receiving optical signals, and said first active area of said first transducer being optically coupled to the first end of said scintillator crystal;
   a second transducer for receiving another of the plurality of optical signals from said scintillator crystal and converting the another of the plurality optical signals to a second electrical signal, said second transducer positioned closer to the photon source than the at least one first transducer and having a second active area for receiving optical signals and said second active area of said second transducer being optically aligned for receiving optical signals from a second end of said scintillator crystal;
   an optical guide, said optical guide optically coupled between said second end of said scintillator crystal and said active area of said second transducer, said optical guide being conducive to direct optical signals to said active area of said second transducer; and
   a computer array electrically coupled to said at least one first transducer to receive said first electrical signal for generating a centriod for determining the x-position and the y-position of the interaction site, and to said second transducer for receiving said second electrical signal for determining said z-position from said second electrical signal,
   wherein said at least one first transducer and the second transducer have a M:1 correspondence, where M is equal to one or more.

2. The detector assembly recited in claim 1 above, wherein said first active area is larger than said second active area.

3. The detector assembly recited in claim 1 above, wherein said scintillator crystal further comprises:
   a plurality of slits, each of said plurality of slits being approximately equal in length and terminating within said crystal between said first end and said second end.

4. The detector assembly recited in claim 1 above, wherein said second transducer further comprises:
   a semiconducting material in a thickness such that said second transducer has a low photon absorption rate and a low photon scattering rate.

5. The detector assembly recited in claim 4 above, wherein said second transducer is one of a photodiode and an avalanche photodiode (APD).

6. The detector assembly recited in claim 4 above, wherein said second transducer is an avalanche photodiode (APD).

7. The detector assembly recited in claim 5 above, wherein said first transducer is a photomultiplier (PMT).

8. The detector assembly recited in claim 1 above further comprises:
   a third transducer for receiving one of the plurality of optical signals from said scintillator crystal and converting the one of the plurality of optical signals to a third electrical signal, said third transducer having a third active area for receiving optical signals, and said third active area of said third transducer being optically coupled to the first end of said scintillator crystal.

9. The detector assembly recited in claim 8 above, wherein said first and third transducers are photomultipliers (PMT) and said second transducer is an avalanche photodiode (APD).

10. The detector assembly recited in claim 9 above, wherein said scintillator crystal being optically coupled between a plurality of optical guides and a plurality of photomultipliers (PMT).

11. The detector assembly recited in claim 1 above, wherein said scintillator crystal further comprises:
    a bismuth germanate (BGO) crystal.

12. The detector assembly recited in claim 1 above, wherein said scintillator crystal further comprises:
    a plurality of bismuth germanate (BGO) crystals.

13. The detector assembly recited in claim 1 above, wherein said scintillator crystal further comprises:
    a sodium iodate (NaI) crystal.

14. The detector assembly above in claim 1 recited, wherein said scintillator crystal further comprises:
    a plurality of sodium iodate (NaI) crystals.

15. The detector assembly above in claim 1 recited, wherein a distance between said first and second ends exposes an oblique angle to a photon.

16. The detector assembly of claim 1, wherein M equals one.

17. The detector assembly of claim 1, wherein said scintillator crystal is a single crystal coupled to a plurality of first sensors and a plurality of second sensors.

18. The detector assembly of claim 1, wherein said scintillator crystal further comprises:
    a lateral dimension that is larger than a corresponding lateral dimension of said second transducer; and
    a plurality of slits extending from said second end of said scintillator crystal in a direction substantially perpendicular to the lateral dimension of the scintillator crystal.

* * * * *